US008286486B2

(12) United States Patent
Mutharasan et al.

(10) Patent No.: US 8,286,486 B2
(45) Date of Patent: Oct. 16, 2012

(54) MOLECULAR CONTROL OF SURFACE COVERAGE

(75) Inventors: Rajakkannu Mutharasan, West Chester, PA (US); David L. Delesdernier, Kennett Square, PA (US); Kishan Rijal, Harleysville, PA (US)

(73) Assignee: Drexel University, Philadelphia, PA (US)

( * ) Notice: Subject to any disclaimer, the term of this patent is extended or adjusted under 35 U.S.C. 154(b) by 640 days.

(21) Appl. No.: 12/299,841

(22) PCT Filed: May 10, 2007

(86) PCT No.: PCT/US2007/011280

§ 371 (c)(1), (2), (4) Date: Apr. 14, 2009

(87) PCT Pub. No.: WO2007/133619
PCT Pub. Date: Nov. 22, 2007

(65) Prior Publication Data

US 2010/0018310 A1 Jan. 28, 2010

Related U.S. Application Data

(60) Provisional application No. 60/746,948, filed on May 10, 2006.

(51) Int. Cl.
*G01H 13/00* (2006.01)

(52) U.S. Cl. .......................................................... 73/579

(58) Field of Classification Search .................... 73/579, 73/61.75, 73, 61.49, 24.01, 580, 64.53
See application file for complete search history.

(56) References Cited

U.S. PATENT DOCUMENTS

| | | | |
|---|---|---|---|
| 4,186,599 | A | 2/1980 | Frick |
| 4,791,818 | A | 12/1988 | Wilde et al. |
| 5,116,759 | A | 5/1992 | Klainer et al. |

(Continued)

FOREIGN PATENT DOCUMENTS

EP 0631319 A1 12/1994

(Continued)

OTHER PUBLICATIONS

Campbell, G.A., et al., "Method of Measuring *Bacillus anthracis* spores in the presence of copious amounts of *Bacillus thuringiensis* and *Bacillus cereus*," Anal. Chem., published online Dec. 22, 2006, 79(3), 1145-1152.

(Continued)

*Primary Examiner* — Peter Macchiarolo
*Assistant Examiner* — Tamiko Bellamy
(74) *Attorney, Agent, or Firm* — Woodcock Washburn, LLP

(57) ABSTRACT

The concentration of a material covering a surface is controlled via an equilibrium process. Equilibrium parameters such as a concentration of the provided material, the exposure time of the material to the surface, and the surface area of an attractor applied to the surface are determined utilizing a millimeter sized piezoelectric cantilever sensor. In an example embodiment, the material is provided at a low concentration to the surface until equilibrium is attained. The amount of material accumulated on the surface is determined utilizing the cantilever sensor. The surface area of the attractor and the measured amount of material are utilized to determine the amount of the attractor surface area having the material bound thereto. Knowledge of the equilibrium parameters allows controlled surface coverage of the material on the attractor for any application. The concentration of the material adsorbed on the surface is precisely determinable and repeatable.

25 Claims, 15 Drawing Sheets

12

U.S. PATENT DOCUMENTS

| | | | |
|---|---|---|---|
| 5,445,008 | A | 8/1995 | Wachter et al. |
| 5,583,300 | A | 12/1996 | Green et al. |
| 5,719,324 | A | 2/1998 | Thundat et al. |
| 6,170,981 | B1 | 1/2001 | Regnier et al. |
| 6,274,723 | B1 | 8/2001 | Nilsen |
| 6,336,366 | B1 | 1/2002 | Thundat et al. |
| 6,543,274 | B1 | 4/2003 | Herrmann et al. |
| 6,589,727 | B1 | 7/2003 | Kleneman et al. |
| 6,880,402 | B1 | 4/2005 | Couet et al. |
| 6,906,450 | B2 * | 6/2005 | Tamayo De Miguel et al. ............................ 310/317 |
| 7,195,909 | B2 | 3/2007 | Kleneman et al. |
| 7,263,874 | B2 | 9/2007 | Fitch et al. |
| 7,458,265 | B2 * | 12/2008 | Shih et al. ...................... 73/579 |
| 7,892,759 | B2 * | 2/2011 | Mutharasan et al. .......... 435/7.1 |
| 2003/0194697 | A1 | 10/2003 | Kleneman et al. |
| 2003/0224551 | A1 | 12/2003 | Kim et al. |
| 2005/0016276 | A1 * | 1/2005 | Guan et al. ...................... 73/579 |
| 2005/0063882 | A1 | 3/2005 | Centanni et al. |
| 2005/0112621 | A1 | 5/2005 | Kim et al. |
| 2005/0164299 | A1 | 7/2005 | Stewart |
| 2005/0229677 | A1 | 10/2005 | Tuller et al. |
| 2005/0277852 | A1 | 12/2005 | Shih et al. |
| 2006/0053870 | A1 | 3/2006 | Berndt |
| 2006/0160098 | A1 | 7/2006 | Zak et al. |
| 2006/0196253 | A1 | 9/2006 | Crawley et al. |
| 2006/0198760 | A1 * | 9/2006 | Potyrailo et al. ........... 422/82.01 |
| 2006/0223171 | A1 | 10/2006 | Craighead et al. |
| 2006/0228657 | A1 | 10/2006 | Masters et al. |
| 2007/0089515 | A1 | 4/2007 | Shih et al. |
| 2007/0169553 | A1 | 7/2007 | Mutharasan et al. |
| 2007/0218534 | A1 | 9/2007 | Kleneman et al. |
| 2008/0034840 | A1 | 2/2008 | Mutharasan et al. |
| 2008/0035180 | A1 | 2/2008 | Mutharasan et al. |
| 2009/0078023 | A1 | 3/2009 | Mutharasan et al. |

FOREIGN PATENT DOCUMENTS

| | | |
|---|---|---|
| EP | 1536227 A2 | 6/2005 |
| WO | 98/50773 A2 | 11/1998 |
| WO | 2005/043126 A2 | 5/2005 |

OTHER PUBLICATIONS

Campbell, G.A., et al., "*Escherichia coli* O157:H7 detection limit of millimeter-sized PZT cantilever sensors in 700 cells/mL," Analytical Sci., Apr. 2005, 21, 11-13.

Campbell, G.A., et al., "Detection of pathogen *Escherichia coli* O157:H7 using self-excited PZT-glass microcantilevers," Biosensors and Bioelectronics, Sep. 15, 2005, Epub Dec. 21, 2004, 21(3), 462-473.

Campbell, G.A., et al., "Detect of *Escherichia coli* O157:H7 in ground beef samples using piezoelectric excited millimeter-sized cantilever (PEMC) sensors," Biosens Bioelectron, Feb. 15, 2007, Epub Jul. 10, 2006, 22(7), 1296-1302.

Campbell, G.A., et al.,"A method of measuring *Escherichia coli* O157:H7 at 1 cell/mL in 1 liter sample using antibody functional piezoelectric-excited millimeter-sized cantilever sensor," Environ. Sci. Technol., published online Jan. 23, 2007, 41(5), 1668-1674.

Campbell, G.A., et al., "Detection and quantification of proteins using self-excited PZT-glass millimeter-sized cantilever," Biosensors and Bioelectronics, 2005, 21, 597-607.

Campbell, G.A., et al., "Piezoelectric-excited millimeter-sized cantilever (PEMC) sensors detect *Bacillus anthracis* at 300 spores/mL," Biosensors Bioelectronics, 2006, 21, 1684-1692.

Campbell, G.A., et al., "Detection of *Bacillus anthracts* spores and a model protein using PEMC sensors in a flow cell at 1 mL/MIN," Biosens Bioelectron, Jul. 15, 2006, Epub Jan. 19, 2006, 22(1), 78-85.

Campbell, G.A., et al., "Detection of airborne *Bacillus anthracis* spores by an integrated system of an air sampler and a cantilever immunosensor," Sensors and Actuators B Chemical, Nov. 15, 2007, available online May 1, 2007, 127(2), 376-382.

Campbell, G.A., et al., "PEMC sensor's mass change sensitivity in 20 PG/HZ under liquid immersion," Biosensors and Bioelectronics, Jul. 15, 2006, Epub Jan. 18, 2006, 22(1), 35-41.

Campbell, G.A., et al., "Use of Piezoelectric-Excited Millimeter-Sized Cantilever Sensors to Measure Albumin Interaction with Self-Assembled Monolayers of Alkanethiols Having Different Functional Headgroups," Anal. Chem., available online Feb. 28, 2006, 78(7), 2328-2334.

Carr, D.W., et al., "Fabrication of nanoelectromechanical systems in single crystal silicon using silicon on insulator substrates and electron beam lithography," J. Vac. Sci. Technology, B, 15(6), 2760-2763.

Maraldo, D., et al., "Method for Quantification of a Prostate Cancer Biomarker in Urine without Sample Preparation," Analytical Chem., Available online Sep. 15, 2007, 79(20), 7683-7690.

Maraldo, D., et al., "Preparation-free method for detecting *Escherichia coli* O157:H7 in the presence of spinach, spring lettuce mix, and ground beef particulates," J. of Food protection, Nov. 2007, 70(11) 2651-2655.

Maraldo, D., et al., "Detection and confirmation of staphylococcal enterotoxin B in apple juice and milk using Piezoelectric-excited Millimeter-sized cantilever (PEMC) sensors at 2.5 femtograms/mL," Analytical Chem., 2007, 79(20) 7636-7643.

Maraldo, D., et al., "10-minute assay for detecting *Escherichia coli* O157:H7 in ground beef samples using piezoelectric-excited millimeter-sized cantilever (PEMC) sensors," J. of Food Protection, 2007, 70(7), 1670-1677.

Maraldo, D. et al., "Method for Label-Free Detection of Femtogram Quantities of Biologics in Flowing Liquid Samples," Anal. Chem., Apr. 1, 2007, 79(7), 2762-2770.

Rijal, K., et al., "PEMC-based method of measuring DNA hybridization at femtomolar concentration directly in human serum and in the presence of copious non-complementary strands," Analytical Chem., 2007, 79, 7392-7400.

Rijal, K., et al., "A method for measuring self-assembly of alkanethiols on gold at femtomolar concentrations," Langmuir, 2007, 23, 6856-6863.

Seung S. Lee, et al., "Self-excited piezoelectric cantilever oscillators," Transducers '95—Eurosensors IX, The 8$^{th}$ Int. Conf. on Solid-State Sensors and Actuators, and Eurosensors IX, Stockholm, Sweden, Jun. 25-29, 1995, 417-420.

Wilson, L., et al., "Viscosity and density values from excitation level response of piezoelectric-excited cantilever sensors," Sensors and Actuators A, Jul. 20, 2007, 138, 44-51.

Yi Jeong W. et al., "In situ cell detection using piezoelectric lead zirconate titanate-stainless steel cantilevers," J Applied Physics, Jan. 1, 2003, 93(1), 619-625.

Zhou J. et al., "Zeolite-modified microcantilever gas sensor for indoor air quality control," Sensors and Actuators B, Oct. 1, 2003, 94(3), 337-342.

U.S. Appl. No. 11/747,183 by Mutharasan, et al., filed May 10, 2007.
U.S. Appl. No. 12/130,446 by Mutharasan, et al., filed May 30, 2008.
U.S. Appl. No. 12/141,846 by Mutharasan, et al., filed Jun. 18, 2008.
U.S. Appl. No. 60/746,948 by Mutharasan, filed May 10, 2006.
U.S. Appl. No. 60/746,951 by Mutharasan, et al., filed May 10, 2006.
U.S. Appl. No. 60/807,020 by Mutharasan, et al., filed Jul. 11, 2006.
U.S. Appl. No. 60/944,592 by Mutharasan, filed Jun. 18, 2007.
U.S. Appl. No. 60/954,488 by Mutharasan, filed Aug. 7, 2007.

* cited by examiner

| PEMC | Resonant frequency in air kHz | Q factor in air | Resonant frequency in ethanol kHz | Q factor in ethanol |
|---|---|---|---|---|
| A | 843.25 ± 0.25 | 68 ± 1 | 786.50 ± 0.25 | 49 ± 1 |
| B | 852.75 ± 0.25 | 61 ± 1 | 795.25 ± 0.25 | 44 ± 1 |
| C | 858.20 ± 0.20 | 72 ± 1 | 805.00 ± 0.20 | 48 ± 1 |

MOLECULAR CONTROL OF SURFACE COVERAGE

CROSS-REFERENCE TO RELATED APPLICATIONS

This application is the National Stage of International Application No. PCT/US2007/011280, filed May 10, 2007, which claims the benefit of U.S. Provisional Application No. 60/746,948 filed May 10, 2006, the disclosures of which are incorporated herein by reference in their entireties.

TECHNICAL FIELD

The technical field generally relates to controlling the amount of surface coverage obtained in an equilibrium coating process, and more specifically relates to controlling the concentration of the coating material in a coating solution used to coat the surface.

BACKGROUND

Typical methods of applying coatings to achieve partial surface coverage of a surface use a timed reaction rate process wherein the surface is contacted with the coating material for a predetermined time sufficient to achieve the desired portion of surface coverage. Such methods however, suffer from difficulties in that they are not consistently repeatable and the results are not as precise as may be required for specific applications.

SUMMARY

The concentration of a material covering a surface is controlled via an equilibrium process. The concentration of the material adsorbed on the surface is precisely determinable and repeatable. In an example embodiment, the material is provided at a low concentration with respect to the amount of material that can be adsorbed by the surface. Control of the amount of surface coverage is obtained by controlling the concentration of the coating material in a coating solution used to coat the surface and the exposure time of the material to the surface.

In an example embodiment, a millimeter sized piezoelectric cantilever sensor is utilized to determine equilibrium parameters between a material and a surface to which it is applied. A surface of the sensor is exposed to the material until equilibrium is established in a molecular reaction between the surface and the material. The surface comprises a surface of a non-piezoelectric portion of the sensor. Equilibrium is determined, via the sensor, in accordance the amount of mass of the material accumulated on the surface. The equilibrium parameters include the concentration of the material be provided and the exposure time.

Accordingly, the equilibrium parameters can be utilized to control the concentration of surface coverage of a material on a surface. Thus, the concentration of surface coverage of any appropriate material on any appropriate surface can be controlled via the concentration of the applied material and the exposure time of the material to the surface. In an example embodiment, a surface can be partially coated by contacting the surface with a coating solution under conditions such that a concentration of coating material in the coating solution is insufficient to coat the entire surface under the coating conditions. A multi-step coating process can be performed wherein two or more sequential coating steps are employed. The second or a subsequent coating step results in coating of all or part of the surface portion that remains uncoated by previous coating steps. One or more subsequent surface treatment steps can be implemented to alter one or more aspects of the applied coating or coatings.

BRIEF DESCRIPTION OF THE DRAWINGS

The foregoing summary, as well as the following detailed description, is better understood when read in conjunction with the appended drawings. For the purpose of illustrating a self-exciting, self-sensing piezoelectric cantilever sensor, there is shown in the drawings exemplary constructions thereof; however, a self-exciting, self-sensing piezoelectric cantilever sensor is not limited to the specific methods and instrumentalities disclosed.

FIG. 12 is a table of resonance frequency characteristics of three piezoelectric-excited millimeter-sized cantilever (PEMC) sensors used in an experiment.

DETAILED DESCRIPTION OF ILLUSTRATIVE EMBODIMENTS

At low concentrations of coating materials, an equilibrium condition is established between the molecular-surface reaction which results in coating of the surface with the coating material at a calculable concentration. The concentration of the surface coating can be calculated utilizing equilibrium parameters such as the concentration of the material exposed to the surface, the amount of exposure time, and the surface area of an attractor applied to the surface to attract the material. In example embodiments, a millimeter sized piezoelectric cantilever sensor is utilized to determine equilibrium parameters between a material and a surface to which the material is applied. A cantilever sensor is employed to measure the achieved surface equilibrium by determining the weight of coating material that has attached (e.g., adsorbed) to the surface after a given reaction time.

Figure 1:
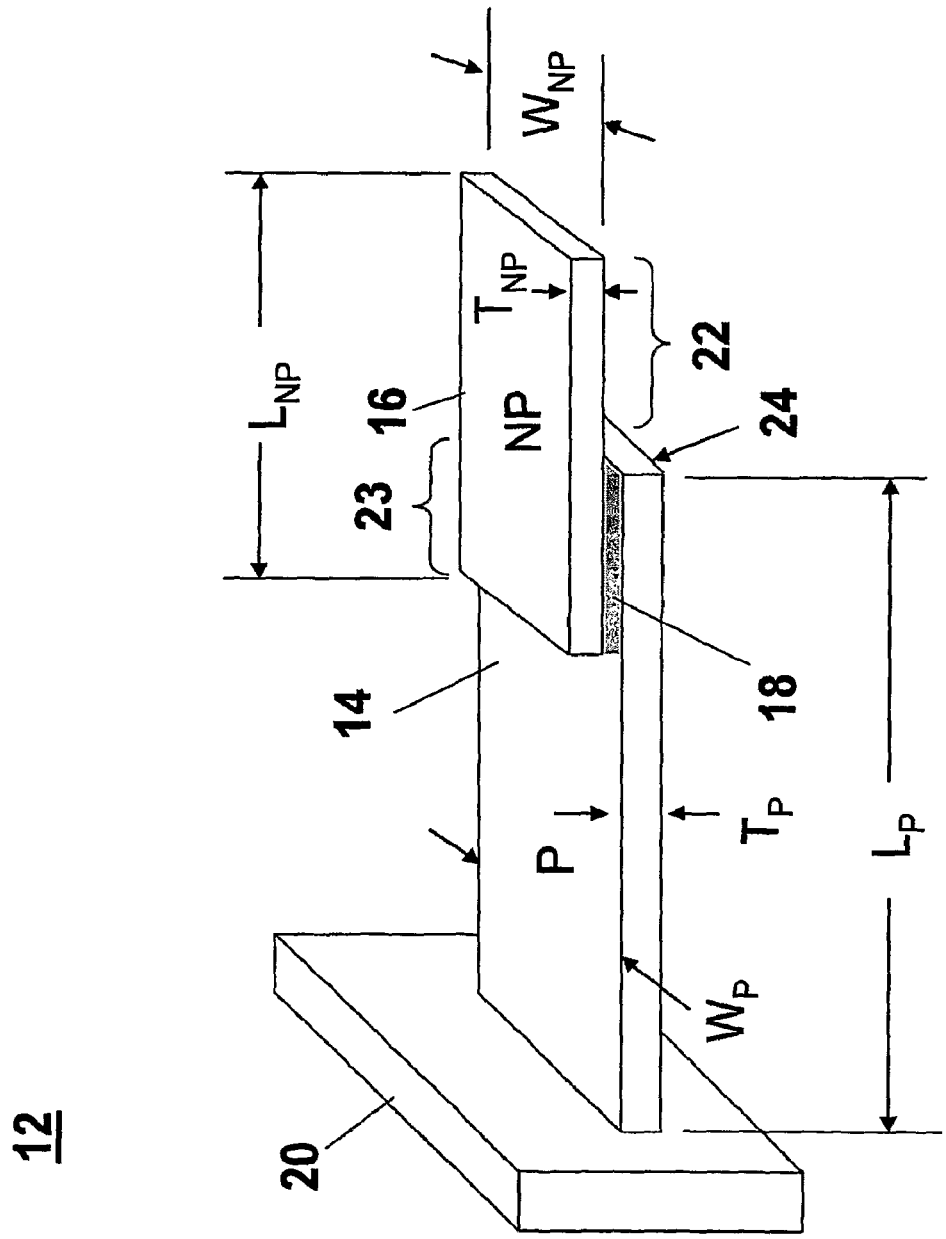
FIG. 1 is an illustration of a self-exciting, self-sensing piezoelectric cantilever sensor 12 configured to determine equilibrium molecular-surface reaction parameters of a material and a surface to which the material is applied.

FIG. 1 is an illustration of a self-exciting, self-sensing piezoelectric cantilever sensor 12 configured to determine equilibrium molecular-surface reaction parameters of a material and a surface to which the material is applied. The self-exciting, self-sensing piezoelectric cantilever sensor 12 comprises a piezoelectric portion 14 and a non-piezoelectric portion 16. Piezoelectric portions are labeled with an uppercase letter p ("P"), and non-piezoelectric portions are labeled with the uppercase letters np ("NP"). The self-exciting, self-sensing piezoelectric cantilever sensor 12 depicts an embodiment of an unanchored, overhang, self-exciting, self-sensing piezoelectric cantilever sensor. The self-exciting, self-sensing piezoelectric cantilever sensor 12 is termed "unanchored" because the non-piezoelectric layer 16 is not attached to the base portion 20. The self-exciting, self-sensing piezoelectric cantilever sensor 12 is termed, "overhang" because the non-piezoelectric layer 16 extends beyond the distal tip 24 of the piezoelectric layer 14 to create an overhanging portion 22 of the non-piezoelectric layer 16. The piezoelectric portion 14 is coupled to the non-piezoelectric portion 16 via adhesive portion 18. The piezoelectric portion 14 and the non-piezoelectric portion overlap at region 23. The adhesive portion 18 is positioned between the overlapping portions of the piezoelectric portion 14 and the non-piezoelectric portion 16. The piezoelectric portion 14 is coupled to a base portion 20.

The piezoelectric portion 14 can comprise any appropriate material such as lead zirconate titanate, lead magnesium niobate-lead titanate solid solutions, strontium lead titanate, quartz silica, piezoelectric ceramic lead zirconate and titanate (PZT), piezoceramic-polymer fiber composites, or the like, for example. The non-piezoelectric portion 16 can comprise any appropriate material such as glass, ceramics, metals, polymers and composites of one or more of ceramics, and polymers, such as silicon dioxide, copper, stainless steel, titanium, or the like, for example.

The self-exciting, self-sensing piezoelectric cantilever sensor can comprise portions having any appropriate combination of dimensions. Further, physical dimensions can be non-uniform. Thus, the piezoelectric layer and/or the non-piezoelectric layer can be tapered. For example, the length (e.g., $L_P$ in FIG. 1) of the piezoelectric portion (e.g., piezoelectric portion 14) can range from about 0.1 to about 10 mm. The length (e.g., $L_{NP}$ in FIG. 1) of the non-piezoelectric portion (e.g., non-piezoelectric portion 16) can range from about 0.1 to about 10 mm. The overlap region (e.g., overlap region 23) can range from about 0.1 to about 10 mm in length. The width (e.g., $W_P$ in FIG. 1) of the piezoelectric portion (e.g., piezoelectric portion 14), and the width (e.g., $W_{NP}$ in FIG. 1) of the non-piezoelectric portion (e.g., non-piezoelectric portion 16), can range from about 0.1 mm to about 4.0 mm. The width (e.g., $W_P$ in FIG. 1) of the piezoelectric portion can differ from the width (e.g., $W_{NP}$ in FIG. 1) of the non-piezoelectric portion as well. The thickness of the (e.g., $T_P$ in FIG. 1) of the piezoelectric portion (e.g., piezoelectric portion 14), and the thickness (e.g., $T_{NP}$ in FIG. 1) of the non-piezoelectric portion (e.g., non-piezoelectric portion 16), can range from about 0.1 mm to about 4.0 mm. The thickness (e.g., $T_P$ in FIG. 1) of the piezoelectric portion also can differ from the thickness (e.g., $T_{NP}$ in FIG. 1) of the non-piezoelectric portion.

Figure 2:
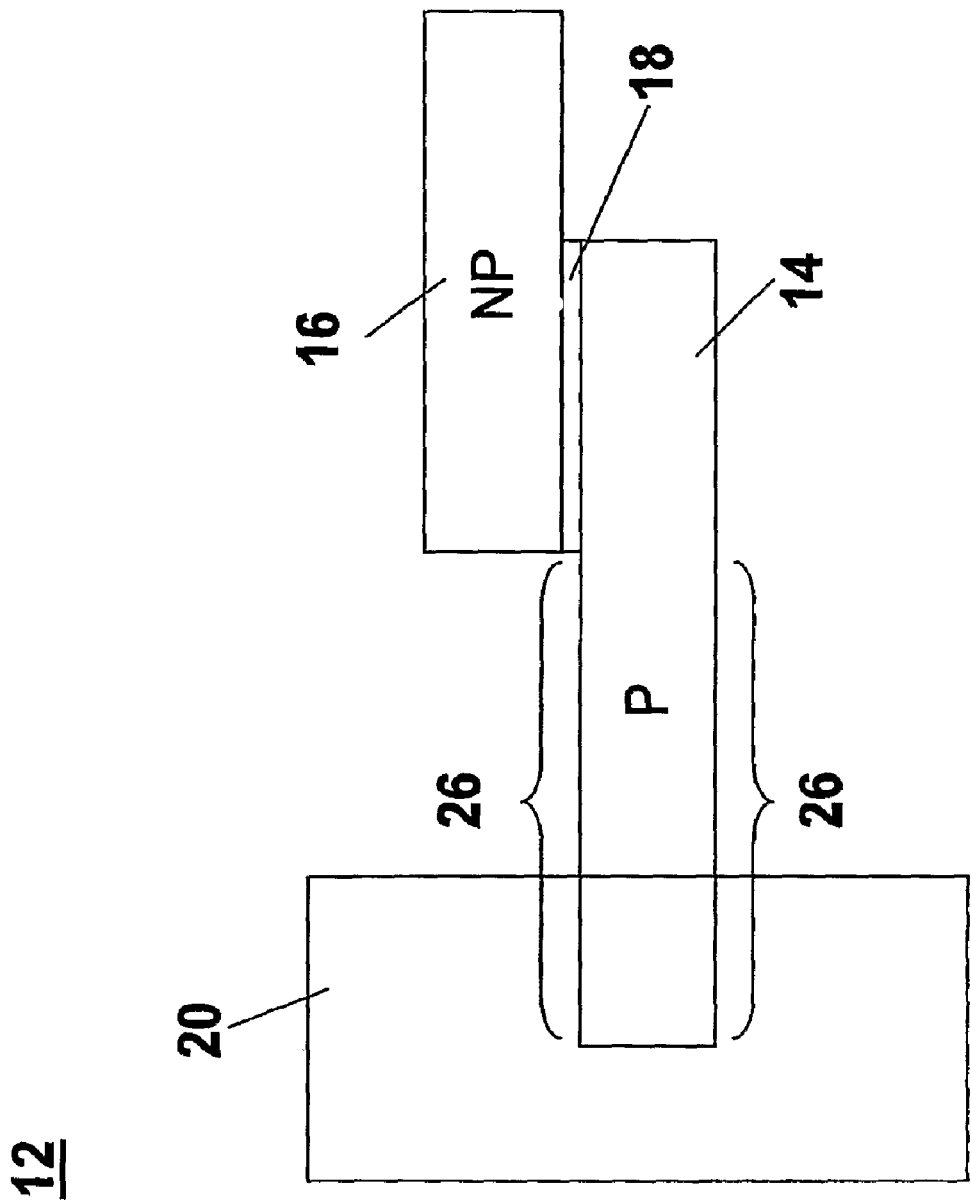
FIG. 2 is a cross-sectional view of an example self-exciting, self-sensing piezoelectric cantilever sensor depicting electrode placement regions for electrodes operationally associated with the piezoelectric layer.
Figure 3:
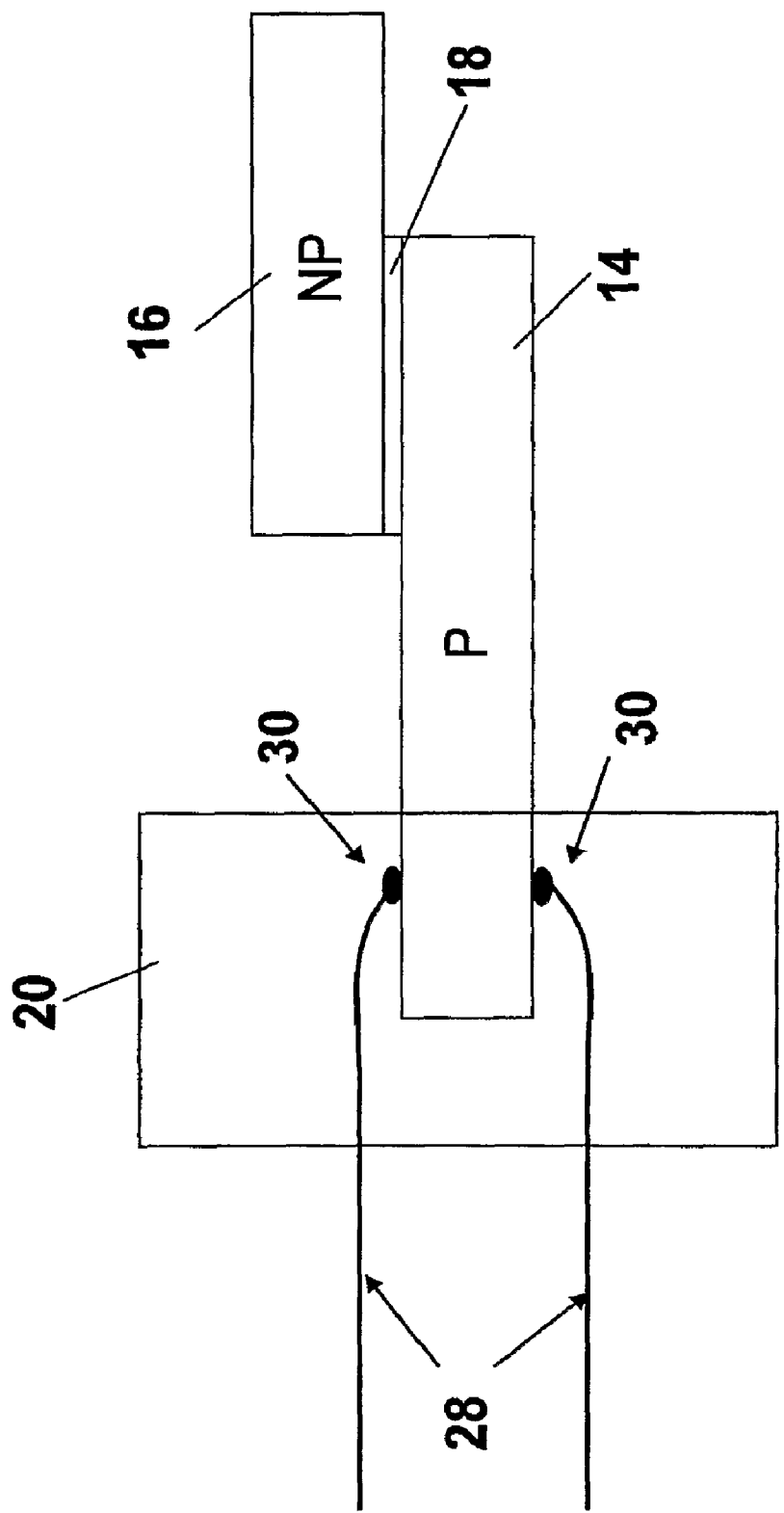
FIG. 3 is a cross-sectional view of an example self-exciting, self-sensing piezoelectric cantilever sensor showing depicting example electrode placement within a base portion of the self-exciting, self-sensing piezoelectric cantilever sensor.
Figure 4:
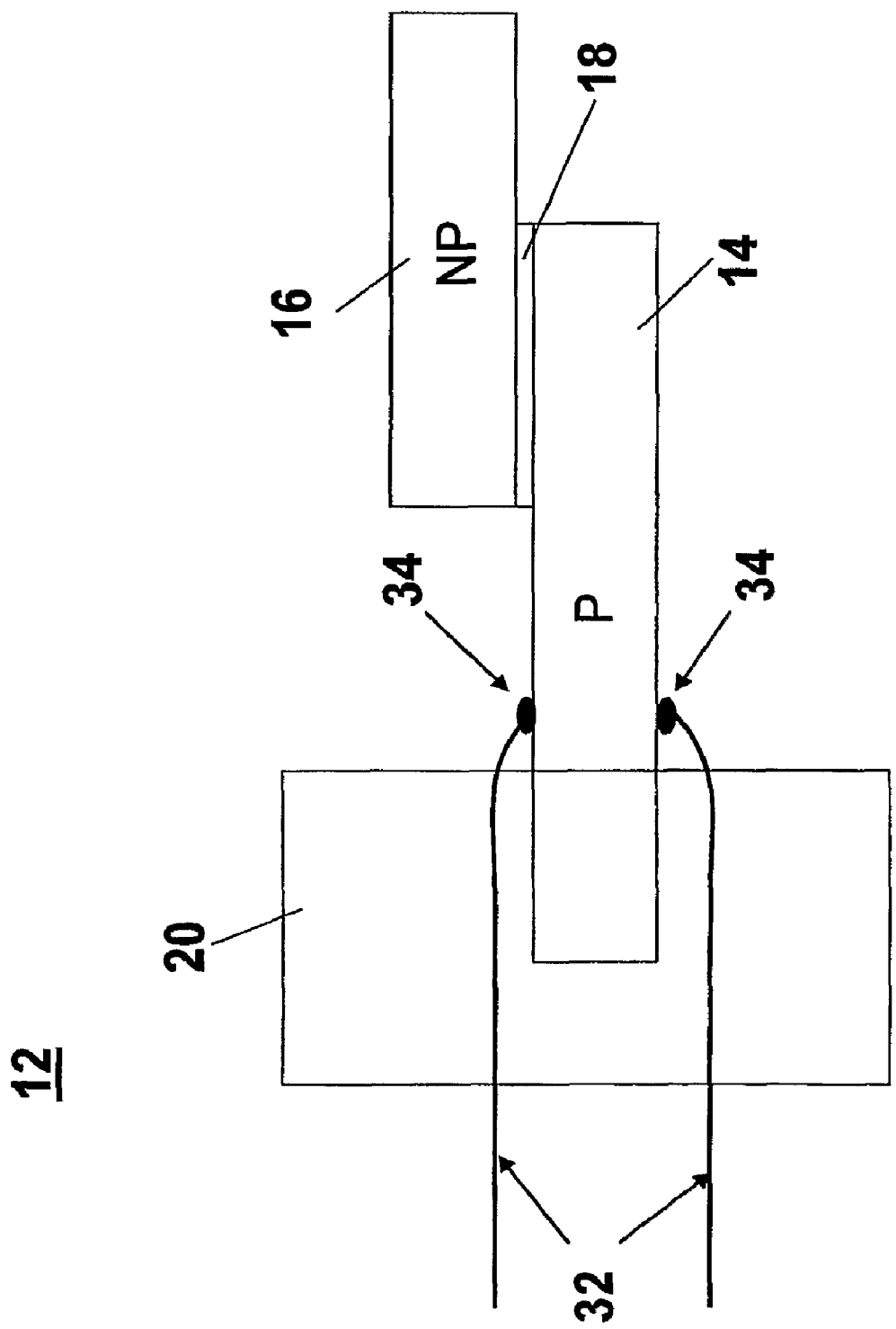
FIG. 4 is a cross-sectional view of an example self-exciting, self-sensing piezoelectric cantilever sensor showing depicting example electrode placement not within a base portion of the self-exciting, self-sensing piezoelectric cantilever sensor.

FIG. 2 is a cross-sectional view of the self-exciting, self-sensing piezoelectric cantilever sensor 12 depicting electrode placement regions 26 for electrodes operationally associated with the piezoelectric portion 14. Electrodes can be placed at any appropriate location on the piezoelectric portion of the self-exciting, self-sensing piezoelectric cantilever sensor as indicated by brackets 26. For example, as shown in FIG. 3, electrodes 28 can be coupled to the piezoelectric portion 14 within the base portion 20. Or, as depicted in FIG. 4, electrodes 32 can be coupled to the piezoelectric portion 14 at any location not within the base portion 20 and not overlapped by the non-piezoelectric portion 16. Electrodes need not be placed symmetrically about the piezoelectric portion 14. In an example embodiment, one electrode can be coupled to the piezoelectric portion 14 within the base portion 20 and the other electrode can be coupled to the piezoelectric portion 14 not within the base portion 20. Electrodes, or any appropriate means (e.g., inductive means, wireless means), can be utilized to provide an electrical signal to and receive an electrical signal from the piezoelectric portion 14. In an example embodiment, electrodes can be coupled to the piezoelectric portion 14 via a bonding pad or the like (depicted as elements 30 in FIG. 3 and elements 34 in FIG. 4). Example bonding pads can comprise any appropriate material (e.g., gold, silicon oxide) capable of immobilization of a receptor material and/or an absorbent material appropriate for use in chemical sensing or for bio-sensing.

Electrodes can be placed at any appropriate location. In an example embodiment, electrodes are operatively located near a location of concentrated stress in the piezoelectric layer 14. As described above, the sensitivity of the self-exciting, self-sensing piezoelectric cantilever sensor is due in part to advantageously directing (concentrating) the stress in the piezoelectric layer 14 and placing electrodes proximate thereto. The configurations of the self-exciting, self-sensing piezoelectric cantilever sensor described herein (and variants thereof) tend to concentrate oscillation associated stress in the piezoelectric layer 14. At resonance, in some of the configurations of the self-exciting, self-sensing piezoelectric cantilever sensor, the oscillating cantilever concentrates stress in the piezoelectric layer 14 toward the base portion 20. This results in an amplified change in the resistive component of the piezoelectric layer 14, and a large shift in resonance frequency at the locations of high stress. Directing this stress to a portion of the piezoelectric layer 14 having a low bending modulus (e.g., more flexible) allows for exploitation of the associated shift in resonance frequency to detect extremely small changes in mass of the self-exciting, self-sensing piezoelectric cantilever sensor. Thus, in example configurations of the self-exciting, self-sensing piezoelectric cantilever sensor, the thickness of the piezoelectric layer 14 located near the base portion 20 is thinner than portions of the piezoelectric layer 14 further away from the base portion 20. This tends to concentrate stress toward the thinner portion of the piezoelectric layer 14. In example configurations, electrodes are located at or near the locations of the oscillation associated concentrated stress near the base portion of the self-exciting, self-sensing piezoelectric cantilever sensor. In other example configurations of the self-exciting, self-sensing piezoelectric cantilever sensor electrodes are positioned proximate the location of concentrated stress in the piezoelectric layer regardless of the proximity of the concentrated stress to a base portion of the self-exciting, self-sensing piezoelectric cantilever sensor.

The self-exciting, self-sensing piezoelectric cantilever sensor can be configured in accordance with a plurality of configurations. Example configurations are described in U.S. patent application Ser. No. 11/625,919, entitled "SELF-EXCITING, SELF-SENSING PIEZOELECTRIC CANTILEVER SENSOR," filed Jan. 23, 2007, which is hereby incorporated by reference in its entirety. It is to be understood however, that the configurations depicted in U.S. patent application Ser. No. 11/625,919, do not represent all possible configurations, but rather a representative sample of configurations of the self-exciting, self-sensing piezoelectric cantilever sensor.

The self-exciting, self-sensing piezoelectric cantilever sensor is utilizable to determine the mass of a material (e.g., analyte) accumulated thereon. In an example embodiment, a portion of the self-exciting, self-sensing piezoelectric cantilever sensor is placed in a medium (e.g., liquid, gas, vacuum). While in the medium, a resonance frequency of the self-exciting, self-sensing piezoelectric cantilever sensor is measured and compared to a baseline resonance frequency. The difference in the measured resonance frequency and the baseline resonance frequency is indicative of an amount of mass of material accumulated (e.g., bound, adsorbed, absorbed) on the self-exciting, self-sensing piezoelectric cantilever sensor. The mass of the material accumulated on the sensing apparatus is utilized to determine the concentration of surface coverage of the material on the surface.

Material can be directly or indirectly bound to the surface of the non-piezoelectric portion of the self-exciting, self-sensing piezoelectric cantilever sensor. Binding of a material to the non-piezoelectric portion of the self-exciting, self-sensing piezoelectric cantilever sensor results in a change in mass of the self-exciting, self-sensing piezoelectric cantilever sensor, a change in stiffness of the self-exciting, self-sensing piezoelectric cantilever sensor, or a combination thereof. The changes in mass and/or stiffness are measurable as changes in resonance frequency, and can be monitored and measured by an appropriate analysis device, such as an operational amplifier, an impedance analyzer, a network analyzer, an oscillator circuit, or the like, for example. Resonance frequency changes, wherein at least a portion of the self-exciting, self-sensing piezoelectric cantilever sensor is immersed in a liquid, gas, and/or a vacuum are detectable and measurable.

The self-exciting, self-sensing piezoelectric cantilever sensor is operateable at high frequencies, such as, on the order of 0.1 MHz. to 6 MHz, for example. At these high frequencies, a Q factor (the ratio of the resonance peak frequency relative to the resonance peak width at half peak height), on the order of 10 to 100, under liquid immersion is obtainable. The self-exciting, self-sensing piezoelectric cantilever sensor is operateable at relative high frequencies in liquid media, gas media, and a vacuum. The self-exciting, self-sensing piezoelectric cantilever sensor thus provides extreme sensitivity to mass changes. The self-exciting, self-sensing piezoelectric cantilever sensor is especially suitable for materials that are present at very low concentrations in media such as in body fluids, water, and food materials, for example.

The self-exciting, self-sensing piezoelectric cantilever sensor described herein provides the ability to detect changes in mass accumulated thereon as small as 1 attogram/Hz ($1 \times 10^{-18}$ grams/Hertz) or less when immersed in a liquid media. Thus, with respect to detecting changes in mass, the self-exciting, self-sensing piezoelectric cantilever sensor is approximately 1 million times more sensitive than a quartz crystal micro-cantilever sensor, approximately 100,000 times more sensitive than standard analytical instruments, and about 1 million times more sensitive than conventional, three-layer piezoelectric cantilever designs.

The self-exciting, self-sensing piezoelectric cantilever sensor permits detection of extremely small concentrations of material that bind to the non-piezoelectric portion thereof. Utilizing the self-exciting, self-sensing piezoelectric cantilever sensor, pathogens and proteins are detectable at concentrations as low as a few pathogens/mL and, for proteins of average size (60 kilo-Daltons, kDa), at less than 1 pathogen/mL. Furthermore, any material that binds to an organic or inorganic functional group on the non-piezoelectric portion is detectable. The self-exciting, self-sensing piezoelectric cantilever sensor is operable in media having relatively high flow rates. The piezoelectric cantilevers sensors is operable in media having flow rates of 0.5 to 10.0 mL/minute, which is approximately 1000 times the flow rate used successfully with known bending mode micro-cantilevers.

The sensitivity of the self-exciting, self-sensing piezoelectric cantilever sensor is due in part to utilizing the piezoelectric layer of the cantilever sensor for both actuation and sensing and the electromechanical properties of the piezoelectric layer of the self-exciting, self-sensing piezoelectric cantilever sensor. At resonance, the oscillating cantilever concentrates stress in the piezoelectric layer toward a base portion of the self-exciting, self-sensing piezoelectric cantilever. This results in an amplified change in the resistive component of the piezoelectric layer, and a large shift in resonance frequency. Directing this stress to a portion of the piezoelectric layer having a low bending modulus (e.g., more flexible) allows for exploitation of the associated shift in resonance frequency to detect extremely small changes in mass of the self-exciting, self-sensing piezoelectric cantilever sensor. For example, if both the piezoelectric layer and the non-piezoelectric layer of a piezoelectric cantilever sensor are anchored at the same end (e.g., potted in epoxy), the sensor is less sensitive to changes in mass because the bending stress in the sensing piezoelectric layer proximal to the anchored end is lower compared to the case when only the piezoelectric layer is anchored. This is because the bending modulus of the two combined layers is higher than the case of anchoring the piezoelectric layer only. Bending modulus is the product of elastic modulus and moment of inertia about the neutral axis. And, moment of inertia is proportional to the cube power of thickness.

For a specific material and surface attractor, equilibrium parameters related to the molecular reaction between the attractor and the material bound thereto are determinable via a millimeter sized piezoelectric cantilever sensor. In an example embodiment, the surface comprises a surface of the non-piezoelectric portion of the cantilever sensor. An attractor is applied to the surface and the material binds to the attractor. The equilibrium parameters can be subsequently used to obtain a desired concentration of the material covering any appropriate surface via an equilibrium process. Thus, the amount of coverage of a surface by specific molecules can be controlled. Further, molecules of different types can be coated in successive steps to produce a surface with varying properties at different locations on the surface. This allows the control of the coating process to be accomplished by "stair stepping" the concentration in increasing amounts to provide the desired ratios of different species on the coating surface.

In an example embodiment, the surface comprises an attractor. The attractor can comprise any appropriate material that exhibits a binding tendency or attraction with the material to be exposed to the surface. An example material can comprise an amine terminated alkane thiol and an example attractor can comprise a <111> gold surface. It is to be understood however, that the herein described surface coating technique is applicable to a variety of materials and surfaces. For example, the technique is applicable to alkyl trichlorosilane self-assembly on hydroxylated surfaces such as oxidized silica, mica, glass and quartz. Octadecyl phosphinic acid can be coated onto mica using the herein described surface coating technique. Also, alkylsiloxanes can be coated onto silicon nitride surfaces using the herein described surface coating technique.

The herein described surface coating technique can be applied to other, similar, coating-substrate systems as well. For example, the various herein described surface coating techniques also can be used in combination with surface masking technologies to lay down patterned surfaces with precise mixtures of different molecules.

Since the coating reaction is heterogeneous between a coating solution and a solid surface, and the reaction occurs at the molecular level, the coated surfaces can be of many different types including planar or curvilinear, smooth or rough and/or various combinations thereof. The process is applicable to liquid-solid, gas-solid and supercritical-solid interfaces and thus solutions of coating materials in gas or supercritical liquids may also be employed in the method of the present invention.

The coating technique described herein is applicable for a variety of applications. For example, the coating technique can be used to apply recognition molecules to the surfaces of detectors for binding species of interest. The technique can also be used in processes for the production of catalysts, membranes, semiconductors and filters.

The herein described coating technique provides the ability to control surface coverage using a controlled equilibrium process instead of a timed reaction rate process, and allows a more precise and repeatable partial surface coverage. The herein described coating technique also allows the production of surfaces with varying properties. The herein described coating technique also permits the use of a mixture of reactant species thereby reducing the number of sequential processing steps that would otherwise be required and hence reducing the time required to process the surface.

Figure 5:
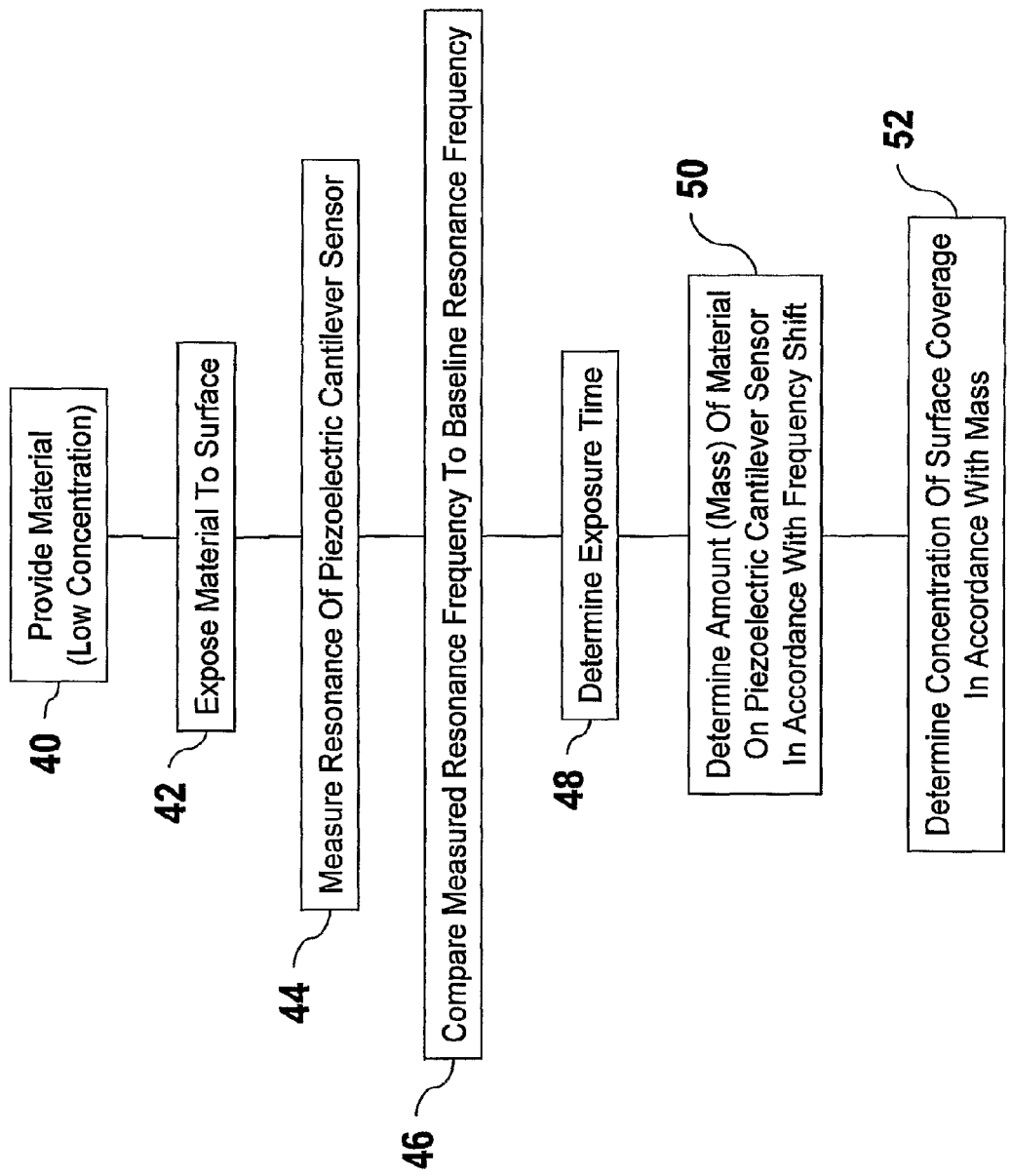
FIG. 5 is a flow diagram of an example process for determining a concentration of surface coverage of a material on a surface.

FIG. 5 is a flow diagram of an example process for determining a concentration of surface coverage of a material on a surface. The material is provided at step 40. In an example embodiment, the material is provided at a concentration that is insufficient to coat the entire surface (e.g., the attractor area) under the coating conditions. The self-exciting, self-sensing piezoelectric cantilever sensor can be configured in accordance with the descriptions provided above, or configured in accordance with any appropriate variant thereof. In an example embodiment, an attractor (e.g., gold) is applied to the non-piezoelectric portion of the sensor. The attractor acts as an attractor to the material to be provided. In an example embodiment, the attractor is specific to a material or group of materials.

The surface is exposed to a material in a medium at step 42. The medium can comprise any appropriate medium, such as a liquid, a gas, a combination of a liquid and a gas, or a vacuum, for example. The medium can exhibit a wide variety of flow conditions. If the material is present in the medium, the material will accumulate on the non-piezoelectric portion of the self-exciting, self-sensing piezoelectric cantilever sensor that has been treated with the attractor. As described above, accumulation (e.g., binding) of the material on the non-piezoelectric portion of the self-exciting, self-sensing piezoelectric cantilever sensor will result in a change in stiffness of the self-exciting, self-sensing piezoelectric cantilever sensor and/or an increase the mass of the self-exciting, self-sensing piezoelectric cantilever sensor, which will decrease the resonance frequency of the self-exciting, self-sensing piezoelectric cantilever sensor.

The resonance frequency of the self-exciting, self-sensing piezoelectric cantilever sensor is measured at step 44. The resonance frequency can be measured by any appropriate means, such as an operational amplifier, an impedance analyzer, a network analyzer, an oscillator circuit, or the like, for example. When the piezoelectric material of the piezoelectric portion of the self-exciting, self-sensing piezoelectric cantilever sensor is excited, the non-piezoelectric portion of the self-exciting, self-sensing piezoelectric cantilever sensor flexes to accommodate the strain caused in the piezoelectric material. When the frequency of excitation is the same as the natural frequency of the underlying mechanical structure, resonance occurs.

The measured resonance frequency is compared to a baseline resonance frequency at step 46. The baseline resonance frequency is the resonance frequency of the self-exciting, self-sensing piezoelectric cantilever sensor having the attractor thereon and no material accumulated thereon. If a difference in frequency (frequency shift) between the measured resonance frequency and the baseline resonance frequency is not measured, it is determined that no material has accumulated on the surface. If a difference in frequency between the measured resonance frequency and the baseline resonance frequency is measured (at step 46), it is determined that material has accumulated on the surface. The amount of time the material has been exposed to the surface is determined at step 48. At step 50, the amount of mass of the material that has accumulated on the non-piezoelectric portion of the self-exciting, self-sensing piezoelectric cantilever sensor is determined in accordance with the frequency shift measured at step 46. At step 52, the concentration of accumulated material is determined. The concentration is determined in accordance the amount of mass determined at step 50, the exposure time determined at step 48, and the amount of attractor on the surface.

Figure 6:
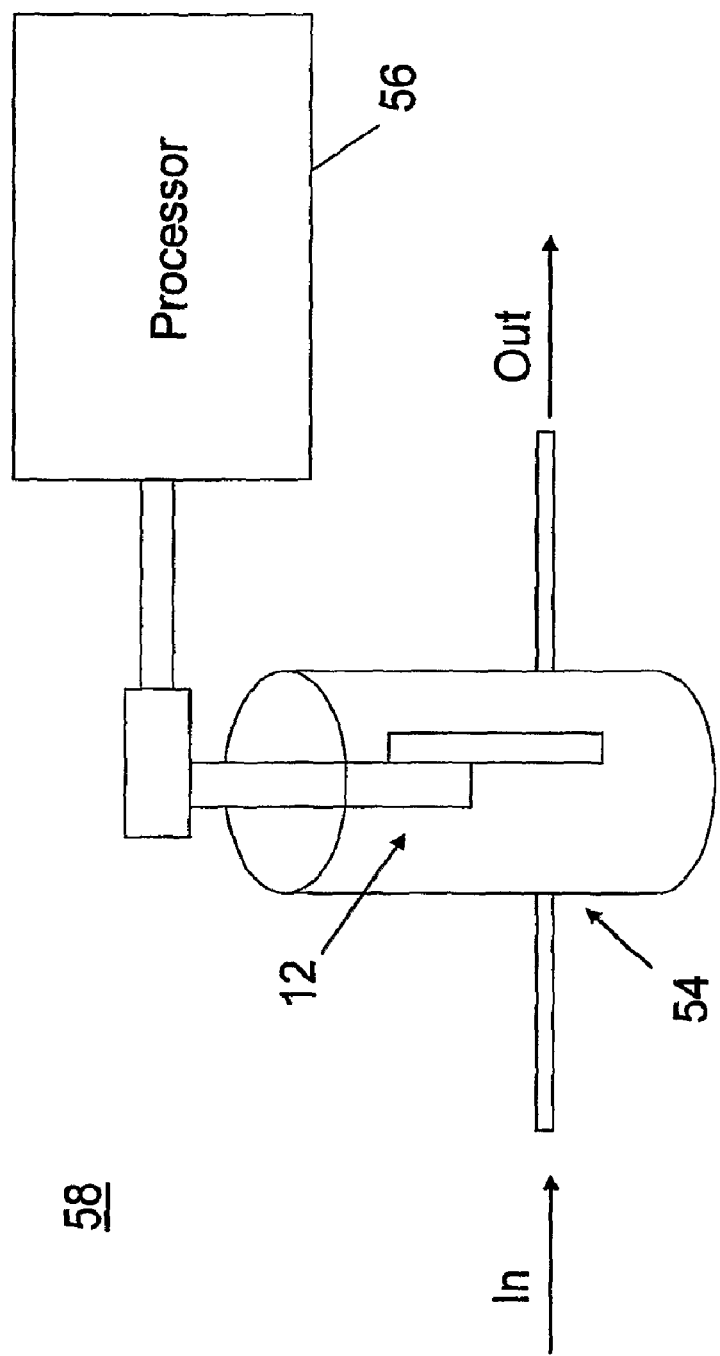
FIG. 6 is an illustration of an example system 58 for determining a concentration of a material on a surface.

FIG. 6 is an illustration of an example system 58 for determining a concentration of a material on a surface. The system 58 comprises a self-exciting, self-sensing piezoelectric cantilever sensor 12, a flow cell 54, and a processor 56. The flow cell 54 functions as an exposing portion of the system 58 for exposing the material to a surface of the self-exciting, self-sensing piezoelectric cantilever sensor 12. The material is provided to the flow cell 54 via an inlet and exits the flow cell 54 via an outlet. The configuration of the flow cell 54 is exemplary, and it not to be limited to the configuration depicted in FIG. 6. The processor 56 is configured to determine a concentration of the material on the surface of the sensor 12 in accordance with an amount of mass of the material accumulated on the surface. The processor 56 is capable of measuring the resonance frequency of the sensor 12; The processor 56 is capable of determining a frequency shift between measured resonance frequencies. For example, the processor 56 is configured to measure a first resonance frequency measure of the piezoelectric cantilever sensor 12 prior to exposure to the material. The processor 56 is capable of measuring a second resonance frequency of the piezoelectric cantilever sensor 12 subsequent to exposure to the material. And the processor 56 is capable of determining determine that a predetermined concentration of the material is on the surface of the piezoelectric cantilever sensor 12 if the second resonance frequency differs from the first resonance frequency by a predetermined amount. The predetermined amount can comprise any appropriate amount indicative of equilibrium.

Various experiments have been conducted to confirm the existence of the herein described equilibrium condition. In the experiments, a self-exciting, self-sensing piezoelectric cantilever sensor was employed to measure the achieved surface equilibrium by measurement of the weight (mass) of coating material that attached to the surface after a given reaction time.

The equilibrium condition resulted in partial coverage of the coating surface even though there was sufficient coating material present in the coating solution to provide complete coverage of the coated surface. Thus, the fact that only part of the surface is coated demonstrates that the coating material is in equilibrium between the coating solution and the surface such that only a portion of the coating material in the coating solution actually coats the surface. Knowledge of the equilibrium parameters thereby allows the desired degree of surface coating to be controlled by selection of the concentration of the coating material in the coating solution since there is a relationship, as shown below in the examples, between the amount of material coated on the surface and the concentration of coating material in the coating solution.

For example, an amine terminated alkane thiol surface coating can be attached to a <111> gold surface using a first coating solution having 1 nM (nanomolar) concentration of amine terminated alkane thiol. Equilibrium is reached in about 20 minutes at a surface coverage of about 5 percent. After washing the surface with a neutral solution, the next reactant for the second coating step can be a carboxylic terminated alkane thiol at 10 nM concentration. After reaching equilibrium in about 20 minutes the surface coverage is now about 10 percent, with about half of the surface coverage provided by the amine terminated alkane thiol and about the other half of the surface coverage provided by the carboxylic terminated alkane thiol. The surface can then be coated in a third step with a methyl terminated alkane thiol at 100 mM (milli-Molar) concentration. The surface is now 20% covered, and the remaining sites could be filled with a filler or by using a coating solution having a sufficiently higher concentration of another functional group containing material to coat the remaining uncoated surface portion.

With near 100% coverage the surface is ready for additional processing by, for example, use of either sequential reactions with the amine, carboxyl and methyl groups, or, for example, by using a blended solution wherein different reactive species for each of the amine, carboxyl and methyl groups are all present in the blended solution. For example, different recognition molecules (e.g., antibodies) can be attached to the coated surface. Or a bi- or multi-layer surface can be produced with varying properties.

The experiments depicted in FIG. 7, FIG. 8, FIG. 9, FIG. 10, and FIG. 11 utilize a self-exciting, self-sensing piezoelectric cantilever sensor with either a fused quartz or a borosilicate glass non-piezoelectric layer. The surface was coated with a thin layer—8 microns—of an epoxy followed by gold sputtered to a thickness of 100 nm (nanometers). The resonance baseline frequency was approximately 850 kHz with a phase angle of nearly 60 degrees. The examples depicted in FIG. 7, FIG. 8, FIG. 9, FIG. 10, and FIG. 11 show that the equilibrium phenomena is present at 1 femtomolar concentrations for thiol binding with a gold surface. The bond associated therewith is a strong bond almost equivalent in energy content to covalent bond.

Figure 7:
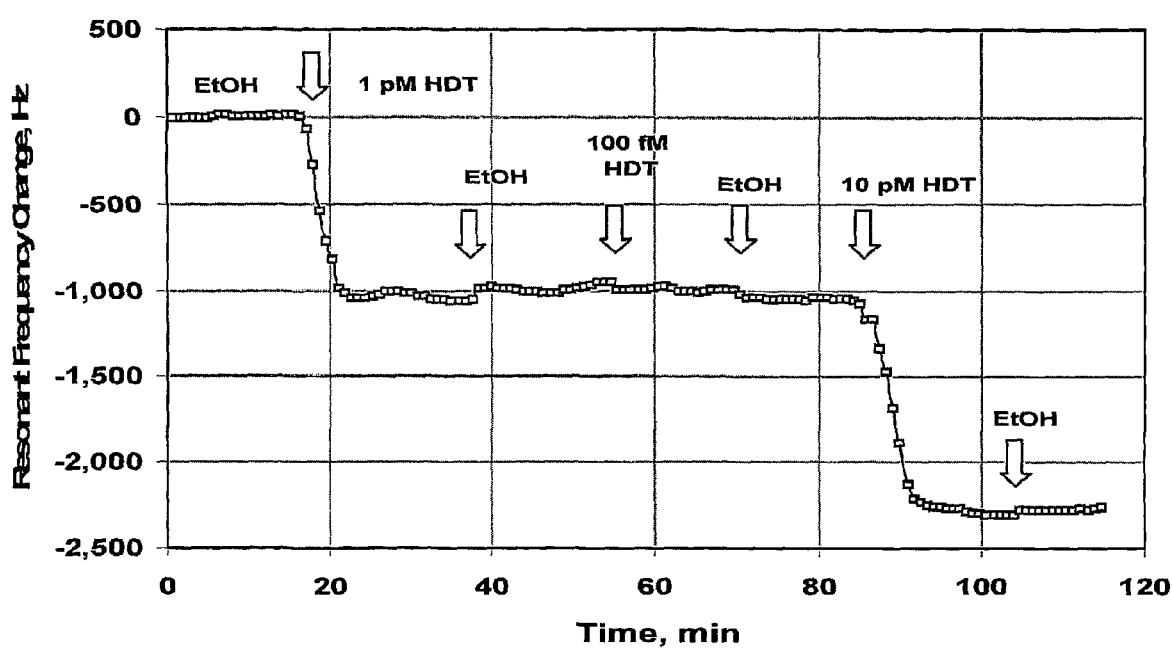
FIG. 7 depicts sequential adsorption of ethanol (EtOH) and 1-hexadecanethiol (HDT) to form a desired monolayer of HDT on a gold coated sensor surface.

FIG. 7 depicts sequential adsorption of ethanol (EtOH) and 1-hexadecanethiol (HDT) to form a desired monolayer of HDT on a gold coated sensor surface. A sequence of steps was used to pattern a gold coated surface with hexanethiols. Initially, to obtain a baseline reading, ethanol was pumped through a flow-cell (FC) containing the piezoelectric cantilever sensor. After obtaining a stable baseline (e.g., about 15 minutes), 1 pM HDT solution was flowed over the surface. 1 pM HDT partially formed a partial monolayer on the gold surface resulting in additional mass attached to the piezoelectric cantilever sensor surface and thus a corresponding drop in resonance frequency of the piezoelectric cantilever sensor. EtOH, 100 fM HDT, and EtOH were again sequentially flowed over the surface of the piezoelectric cantilever sensor, which resulted in no additional monolayer formation on the surface and thus no additional mass attachment or resonance frequency change. When the concentration of HDT flowed across the piezoelectric cantilever sensor was increased to 10 pM, there was additional monolayer formation on the surface and thus a corresponding change in the resonance frequency of the piezoelectric cantilever sensor. Typical noise level was less than 20 Hz. The temperature was maintained at 23.6+0.2° C. and the coating solutions were pumped across the piezoelectric cantilever sensor surface at 0.6 mL/min.

Figure 8:
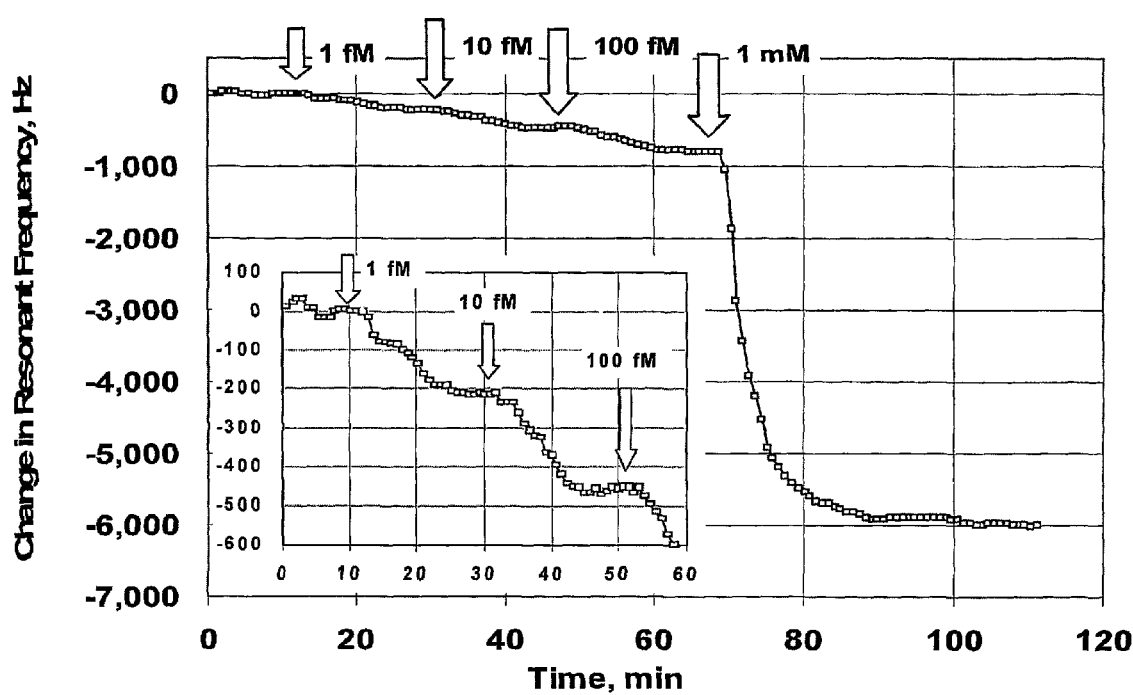
FIG. 8 depicts an experiment wherein patterning of a gold coated surface was performed using very low concentration of 1-hexadecanethiol (HDT).

FIG. 8 depicts an experiment wherein patterning of a gold coated surface was performed using very low concentration of 1-hexadecanethiol (HDT). Similar to the experimental steps described with reference to FIG. 7, but using very low concentrations of HDT, coatings were applied to a gold surface. Increasing the concentration of the HDT in the coating solution from 1 fm, 10 fM and 100 fM of HDT, resulted in very low fractions of surface covered with a monolayer. Complete surface coverage and a large resonance frequency change of the piezoelectric cantilever sensor were achieved by coating with a coating solution having a mM concentration of HDT. Typical noise level was less than 20 Hz. The temperature was maintained throughout the study at 23.6±0.2° C. and the coating solutions were pumped across the piezoelectric cantilever sensor surface at 0.6 mL/min.

Figure 9:
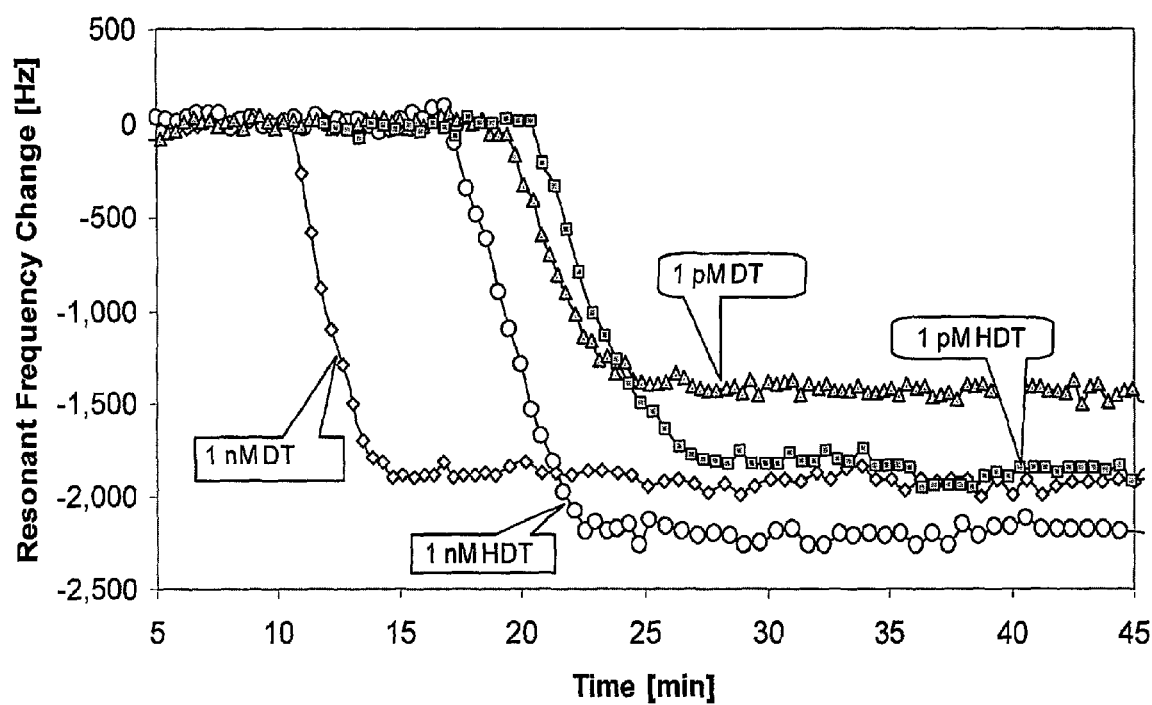
FIG. 9 depicts an experiment conducted using molecules of different chain lengths.

FIG. 9 depicts an experiment conducted using molecules of different chain lengths. The thickness of a hexanethiol pattern formed on a gold coated surface can be manipulated using hexanethiols of various chain lengths. Decanethiol (DT), with a 10 carbon chain length, $M_w$=174 Daltons and 1-hexadecanethiol (HDT) with a 16 carbon chain length, $M_w$=258 Daltons were employed as coating materials. For the same concentrations of these materials, two solutions formed monolayers of similar surface coverage but HDT formed a thicker monolayer as it is a longer chain and thus a heavier molecule. The higher molecular weight of HDT, relative to DT, resulted in a greater mass change on the sensor. Typical noise level was less than 20 Hz. The temperature was maintained throughout the study at 23.6±0.2° C. and the coating solutions were pumped across the piezoelectric cantilever sensor surface at 0.6 mL/min.

Figure 10:
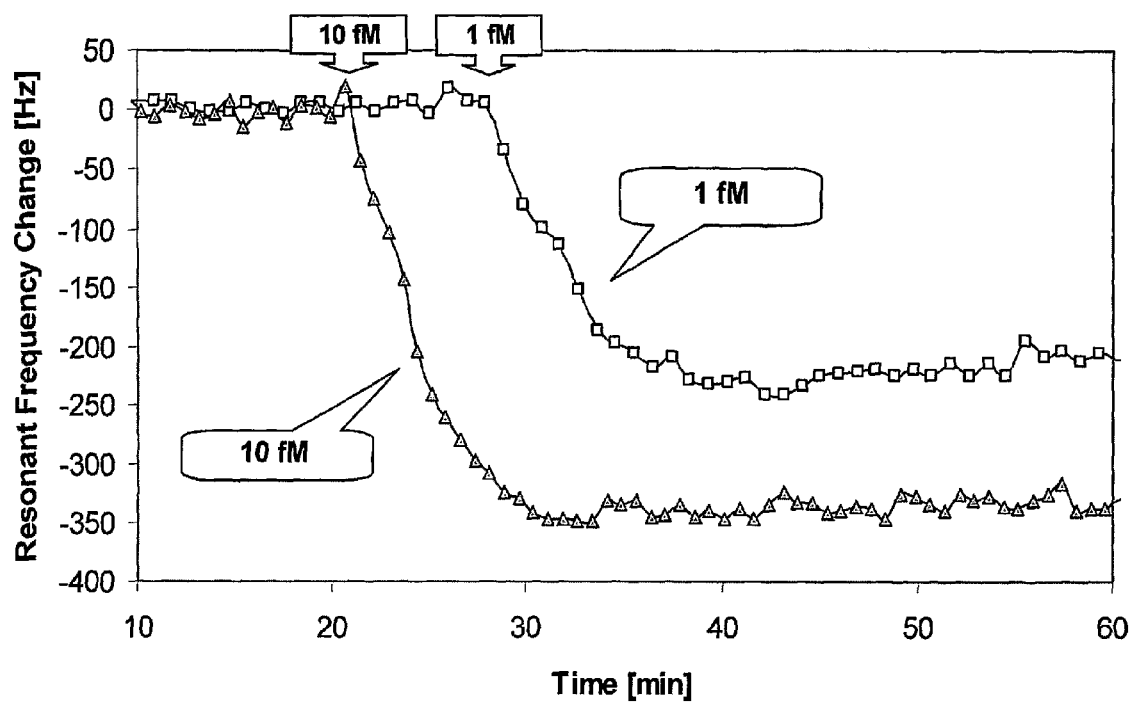
FIG. 10 depicts an experiment wherein 1-Hexadecanethiol coating solutions having concentrations of 1 fM and 10 fM were used to form monolayers on the sensor surface.

FIG. 10 depicts an experiment wherein 1-Hexadecanethiol coating solutions having concentrations of 1 fM and 10 fM were used to form monolayers on the sensor surface. Patterning of a gold surface can be accomplished using hexanethiol concentrations of as low as 1 fm. This enables the formation of a monolayer of very low thickness as well as density. The piezoelectric cantilever sensor was capable of distinguishing mass of monolayers formed from solutions of these two concentrations. Typical noise level was less than 20 Hz. The temperature was maintained throughout the study at 23.6±0.1° C. and the coating solutions were pumped across the sensor surface at 0.6 mL/min.

Figure 11:
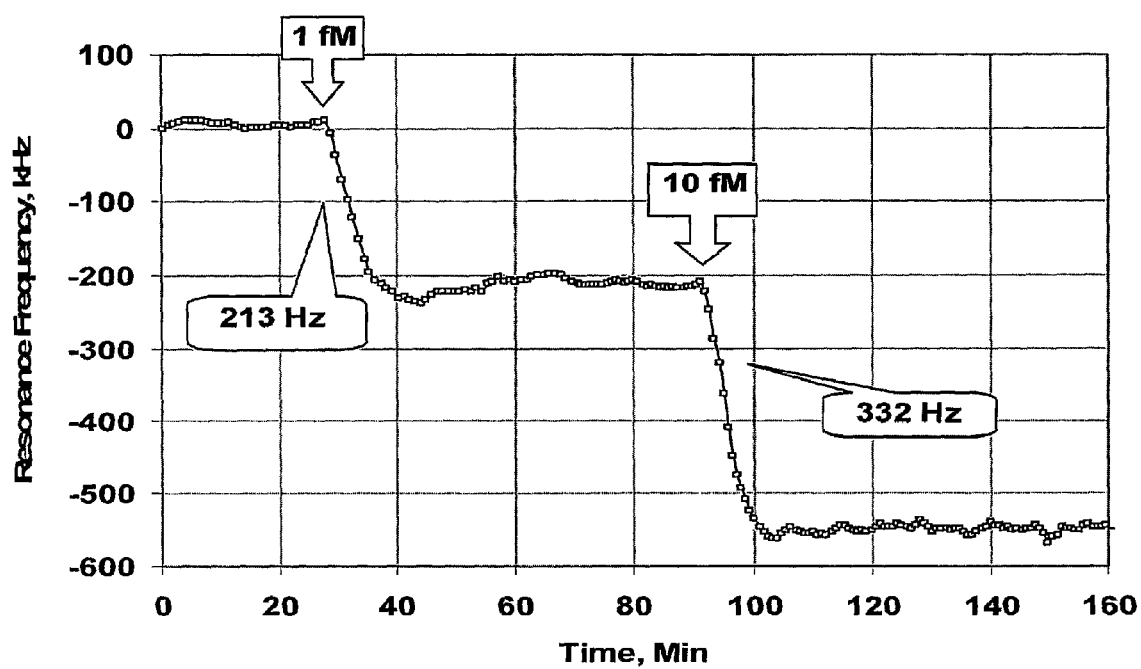
FIG. 11 depicts the sequential attachment of hexadecane thiol at two different concentrations.

FIG. 11 depicts the sequential attachment of hexadecane thiol at two different concentrations. Equilibrium was achieved at a coating solution concentration of 1 fM, and at a subsequent flow of a coating solution concentration of 10 M. The resulting response confirms that additional sites are present on the sensor surface. Typical noise level was less than 20 Hz. The temperature was maintained throughout the study at 23.6±0.1° C. and the coating solutions were pumped across the coating surface at 0.6 mL/min.

Additional experiments were conducted utilizing a gold-coated (2.2 mm$^2$) piezoelectric-excited millimeter-sized cantilever (PEMC) sensor that was exposed to 1-hexadecanethiol (HDT) in ethanol at concentrations ranging from 1 fM to 1 mM, sequentially and separately. A high-order flexural mode at ~850 kHz was monitored during the self-assembly. The resonance frequency decreases due to increased mass as chemisorption occurs on the surface. It was observed that chemisorption of HDT at 1 fM was readily measurable and gave a response of 220±13 Hz (n=4). At higher concentrations (10 fM, 100 fM, 1 pM, 10 pM, 100 pM, 1 nM, 10 nM, 100 nM, 1 μM and 1 mM) the responses were proportionately, but non-linearly, higher. At high concentrations (1 mM) the responses to $C_4$, $C_8$, $C_{11}$, $C_{16}$ and $C_{18}$ alkanethiols were linearly proportional, and was complete in ~25 min. Once the Au-surface is equilibrated at 1 pM, further chemisorption at a lower HDT concentration does not take place, even though over 99% of surface adsorption sites is available. At 1 fM, overall chemisorption rate did not increase with a two-fold increase in HDT flow rate suggesting that chemisorption at 1 fM is not transport-limited. Measured overall chemisorption rate constant at 1 fM was more rapid than 0.1 min$^{-1}$.

The width of the sensor was 1 mm, and the lengths of PZT and glass were 5 and 4 mm, respectively. The glass layer was bonded to PZT in such a way that 1.0±0.11 mm of glass was overhanging off the PZT. The PZT was anchored in a 6-mm glass tube, and the distance between the epoxy end and glass was 0.5±0.1 mm. A 100 nm gold layer was sputtered on both sides of the glass in a Denton Desk II System (Denton Vacuum, New Jersey) at 1 mTorr. The gold film yielded predominantly (>95%) a polycrystalline Au<111> surface as determined by X-ray diffraction.

1-octadecanethiol ($CH_3(CH_2)_{17}SH$, 98%; ODT), 1-hexadecanethiol ($CH_3(CH_2)_{15}SH$, 95%; HDT), 1-undecanethiol ($CH_3(CH_2)_{10}SH$, 98%; UDT), 1-octanethiol ($CH_3(CH_2)_7SH$, 98.5%; OT), 1-butanethiol ($CH_3(CH_2)_3SH$, 99%; BT), sulfuric acid ($H_2SO_4$) hydrogen peroxide ($H_2O_2$) and ethanol (absolute) were from Sigma-Aldrich. Deionized (DI) water was from a Milli-Q plus ultra pure water system (18.2 MΩcm). A stock solution of in M alkanethiol was prepared minutes before an experiment and was used as is, or diluted in ethanol to a lower concentration (40 mL). Prior to each experiment, a gold-sputtered sensor was immersed in ethanol for 5 minutes and then air-dried in a dust-free box. The sensor was regenerated after an experiment by immersing in piranha solution (7:3 volume ratio of $H_2SO_4$ and $H_2O_2$) for 2 minutes and washed with copious amount of DI water, ethanol and then dried.

All experiments were conducted in a flow apparatus, wherein the sensor was firmly secured in a temperature controlled sensor flow cell (SFC; hold up volume 0.3 mL) maintained at 30±0.1° C. The electrodes of the sensor were connected to an impedance analyzer (HP 4192A or HP 4294A) interfaced to a LabVIEW™ data acquisition program. Impedance, capacitance, and phase angle were collected at 1-2 Hz. A typical experiment was started by first flowing pure ethanol through the sensor flow cell until the baseline resonance frequency was stabilized (~5-10 min). At a constant flow rate used (0.6 mL/min), the average bulk velocity in SFC was 0.06 cm/s. After a stable baseline was established, the test solution containing alkanethiol was introduced into the SFC. Each alkanethiol sample (40 mL) was flowed through the SFC in a once-though mode without re-circulation, and the resulting resonance frequency was recorded. Multiple sample chambers were connected to the SFC via a valving arrangement so that samples of different concentrations can be exposed to the sensor in a continuous and systematic manner without stopping flow.

Each experiment described below was repeated a minimum of three times, usually with the same sensor; and, when a sensor was damaged, a different, but similar sensor with a similar resonance property was used. The change in resonance frequency for a given concentration of alkanethiol varied slightly (±8%, n=23) from one sensor to the next depending on differences in resonance peak location. Although several PEMC sensors were fabricated, characterized and used in various experiments, the results obtained with the sensors labeled A, B and C had near-similar resonance spectrum and are summarized in the table of FIG. 12. The modes used for measurement were located at 843.25, 852.75 and 858.20 kHz.

The sensor was cleaned after each experiment as described in the materials and methods section. Our experience shows that cleaning step resulted in a slightly lower frequency response, presumably due to loss of Au<111> sites. Four cleaning steps caused a loss of 8-12% in sensor response. Therefore, to ensure good accuracy and comparison, the sensor was re-coated with Au after three re-uses which gave repeatability within ±6%.

Figure 13A:
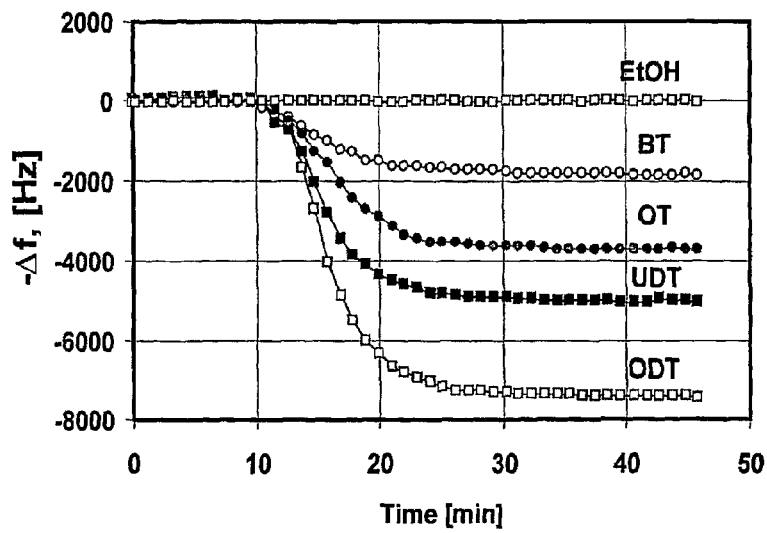
FIG. 13A and FIG. 13B illustrate changes in resonant frequency of a PEMC when exposed to 1 mM alkanethiol solutions of various chain lengths.
Figure 13B:
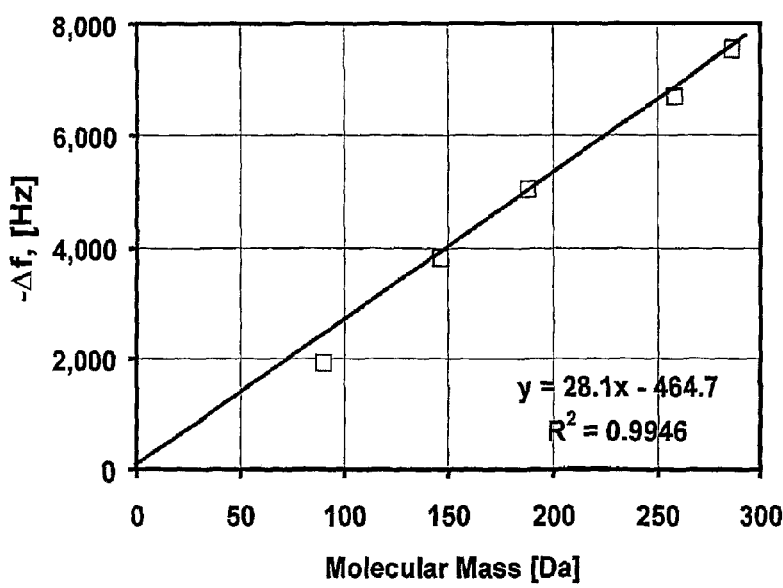

A Au-coated sensor when exposed to high concentration (~mM) alkanethiol solution formed a dense monolayer, wherein the surface density depends on the quality of gold surface, chain length and functional groups of alkanethiol, type of solvent, and temperature. By exposing an Au-coated PEMC sensor to alkanethiol of various molecular masses and known concentrations, the resulting frequency responses can be correlate quantitatively to chemisorbed alkanethiols and related to the changes to chemisorbed mass. Surface area of PEMC A was 2.2 mm$^2$ and thus $1.4 \times 10^{13}$ thiol molecules would form a monolayer, assuming a defect-free surface. Therefore, 40 mL of 1 mM thiol contains more than adequate thiol molecules to form a monolayer. Exposure to 1 mM of 1-butanethiol (BT), 1-octanethiol (OT), 1-undecanethiol (UDT) and 1-octadecanethiol (ODT) resulted in the response shown in FIG. 13A and FIG. 13B. FIG. 13A depicts changes in resonant frequency of PEMC A when exposed to 1 mM alkanethiol solutions of various chain lengths from $C_4$ to $C_{18}$. The frequency response increased with increasing molecular mass. HDT is not shown as it was measured with PEMC B. FIG. 13B depicts the maximum change in resonant frequency to 1 mM alkanethiols plotted against molecular mass. The frequency response is smaller for smaller molecular masses. Note $C_4$ deviates from the straight line that is drawn through the origin and $C_4$, $C_{11}$ and $C_{18}$. So does HDT measured with PEMC B. The response is an exponential decrease followed by a constant resonant frequency. The steady state changes were 0±21 (n=13; only one is shown for clarity), 1,880±170 Hz (n=3), 3,784±310 Hz (n=4), 5,034±340 Hz (n=3) and 7,539±10 Hz (n=3) for ethanol, BT, OT, UDT, and ODT, respectively. Response to HDT was obtained with PEMC B and showed a response of 6,690±430 Hz (n=2) (not shown in FIG. 13A), but the data is part of FIG. 13B. The steady state in FIG. 13A was reached in a fairly short time period of ~25 minutes. It is suspected that the vibrating sensor surface facilitates the chemisorption step. The amplitude of vibration of sensor surface was estimated as a few nm.

As the chain length was increased from $C_4$ to $C_{18}$ the thickness and the mass of the monolayer increased, and there was a near-linear increase in the frequency response. A plot of resonance frequency change against alkanethiol molecular mass yields a straight line as shown in FIG. 13B with a correlation coefficient=0.995, y-intercept=−465 Hz, and indicates that the sensor response is indeed proportional to mass of alkanethiol adsorbed. Closer examination indicated that ODT, UDT and OT lie on a straight line, while BT lies slightly lower than the rest. The line shown in FIG. 13B is a straight line drawn between the origin and the four longer thiols. HDT adsorption value was obtained with PEMC B, and lies slightly below the straight line drawn. The lower position of BT suggests that for shorter alkanethiol, lesser number of BT molecules is chemisorbed than with longer ones at the same thiol concentration.

If n is the number of Au<111> sites per $mm^2$, mass sensitivity can be calculated from $\sigma = An(M/N_A)/(-\Delta f)_{max}$ where $\sigma$ is mass change sensitivity of PEMC, A is Au-coated area, M is molecular mass of alkanethiol, $N_A$ is Avogadro number, and $(\Delta f)_{max}$ is the total change in resonance frequency. For $C_8$ to $C_{18}$ thiols, $\sigma$ values calculated are in the narrow range of 861 to 888 fg/Hz. Even for OT it is quite close to this figure at 887 fg/Hz. For the case of BT, it is significantly lower at 1.1 pg/Hz. These mass sensitivity values are about a thousand-fold lower than what was measured earlier and is due to the nonlinear relationship between sensor response and attached mass, discussed later in the paper. Further, the actual mass sensitivity ($\sigma$) is likely to be lower (meaning more sensitive) than the calculated value due to unaccounted for inherent surface defects.

In order to examine PEMC response to low concentration of alkanethiol, two types of experiments were conducted. In the first, the sensor was exposed to increasing concentration. In the second, alternating high and low concentration exposure was used to examine if desorption would occur. Three cases are described to illustrate the low concentration chemisorption behavior in 1 fM solution. The resonance frequency decreased as soon as HDT solution entered the flow cell. After 15 minutes, the resonance frequency reached a constant value with a decrease of 198±17 Hz, where 17 Hz was the standard deviation over a four minute period. After reaching steady state, the flow was changed to 10 fM HDT and then to 100 fM. The resulting response was a decrease of 266±15 Hz in 13 minutes, followed by a further decrease of 512±16 Hz. That is, 100 fM HDT resulted in a total change of 976±16 Hz. Since the sample was not re-circulated, and equilibrium was reached in 13 minutes, substantial amount of HDT remained in solution. When the flow was changed from 1 fM to 10 fM or from 10 fM to 100 fM, the sensor responded with a decrease in resonance frequency reaching a new steady state. At such a steady state, it is believed that the sample leaving the SFC contains thiol at the same concentration as in the inlet. In other words, the sensor response is proportional to concentration. The response also suggests that there was an increase in the extent of chemisorption as concentration was increased and a new equilibrium was reached between the liquid and surface concentrations. Finally, when 1 mM HDT was pumped in, there was a rapid and sharp large decrease of an additional 5,216±43 Hz with steady state occurring in 22 minutes. The first 90% (~4,800 Hz) of the response occurred in 12 minutes while the remaining 10% required almost the same time period. At this concentration, theoretically the sensor would be covered with a dense SAM (self-assembled monolayer) of HDT. Since PEMC measures mass, no conclusions can be made regarding the structure of SAM.

A sample of 40 mL 1 fM solution contains $2.4 \times 10^7$ thiol molecules. If all the molecules were adsorbed on the 2.2 $mm^2$ Au-coated sensor surface, they would account for less than 0.02% surface coverage. Similarly, the 10 fM and 100 fM HDT solutions would provide for less than 0.2% and 2% surface coverage. Since sensor response reached steady state well short of the 40 mL prepared, the surface coverage was far less than 0.02% and 0.2%. Yet, chemisorbed mass as indicated by frequency response reached a constant value. That is, equilibrium was established between liquid and surface concentrations without reaching full surface coverage.

The time to reach steady state was ~11 minutes in the two cases examined. The fluid lines leading to the flow cell and the flow cell had a hold-up volume of 2.6 and 0.3 mL, respectively. Thus it took ~0.5 minutes to fill the flow cell and ~2-3 minutes to reach homogeneous concentration in the sensor flow cell chamber. The response time observed is believed to be due to the time required to introduce a new concentration into the sensor flow chamber. That is, adsorption mass changes that occur slower than ~0.5 $min^{-1}$ are observable in the apparatus used in the experiment. It is concluded, therefore, that at 1 and 10 fM, the overall chemisorption rate constant is greater than 0.1 $min^{-1}$ In another experiment, PEMC B was initially to 1 pM which caused a decrease of 1,020±29 Hz followed by 1 nM and 1 µM which caused 4,207±31 and 5,011±39 Hz decreases, respectively. Further exposure to 1 mM and finally to ethanol caused no further change in resonance frequency. Final exposure to 1 pM induced no response as well. It is thus concluded that the chemisorbed thiol is not spontaneously released in pure ethanol, and remained on the sensor surface in the time frame of 20-30 minutes. Other experiments of extending the ethanol desoprtion step to two hours caused no measurable change in resonant frequency, and it was concluded that the chemisorption step in ethanol is essentially irreversible once a SAM layer is formed. Similar conclusion was drawn on a QCM using charged thiol in salt solution as solvent.

In order to obtain a higher resolution of the chemisorption step as a function of concentration, PEMC C was exposed to sequentially higher alkanethiol concentration starting at 1 fM to 100 nM in steps of 10× concentration. Results confirm the behavior observed with PEMC A and PEMC B. It was observed that the sensor surface saturates at 10 nM and when exposed to 100 nM, and there was no further decrease in resonance frequency. Since all three sensors had nearly the same surface area (2.2 $mm^2$), it was concluded that 10 nM causes surface saturation, and is consistent with previous results. Since SFC takes ~2-3 minutes to reach homogeneous concentration, it is concluded that chemisorption at 1 fM is rapid, and diffusion effects, if present, were not significant.

Previous experiments illustrated the effects of molecular size at mM concentration which saturates the sensor surface. The sensor's capability to discriminate on molecular mass was also examined by comparing the response to low concentration alkanethiol of two different chain lengths, but at the same molar concentration. Sub-saturation concentrations of 1 pM and 10 pM of DT and HDT were used. First, a 40 mL sample of 1 pM DT was flowed through the sensor in the flow cell. The sensor was cleaned and exposed to 40 mL of 1 pM HDT solution. Similarly, the same sensor was exposed to 10 pM DT and 10 pM HDT solution in a separate experiment. The results indicated that the response to 1 pM DT (1430±21 Hz) was 14% lower than to 1 pM HDT (1730±23). For 10 pM solutions, the change in resonance frequency for HDT was +11% lower (2,210 Hz for HDT vs. 1,950 Hz for DT. Repeat experiments gave similar results with a range of difference of +11 to +13%, indicating a larger resonant frequency decrease for the longer alkanethiol. These results show that for a fixed number of available adsorption sites on gold surface and a fixed number of thiol molecules in the liquid sample, the sensor is capable of discerning chemisorption based on differences in mass of SAM formed on the sensor surface. PEMC B (2.2 mm$^2$), has $1.3 \times 10^{13}$ Au<111> sites. Maximum possible surface coverage from a 40 mL sample of 1 pM HDT or DT is ~0.2%. In another experiment, the sensor reached steady state with less than 10 mL of sample contact. For the case of 40 mL of 10 pM HDT or DT the number of thiol molecules were over 200 times the number of sites on the sensor surface. Although HDT is ~50% heavier than DT, the difference in frequency response was much lower, about one fifth. Based on the these results, it was concluded that the sensor response is proportional to mass of chemisorbed alkanethiol molecules.

Figure 14:
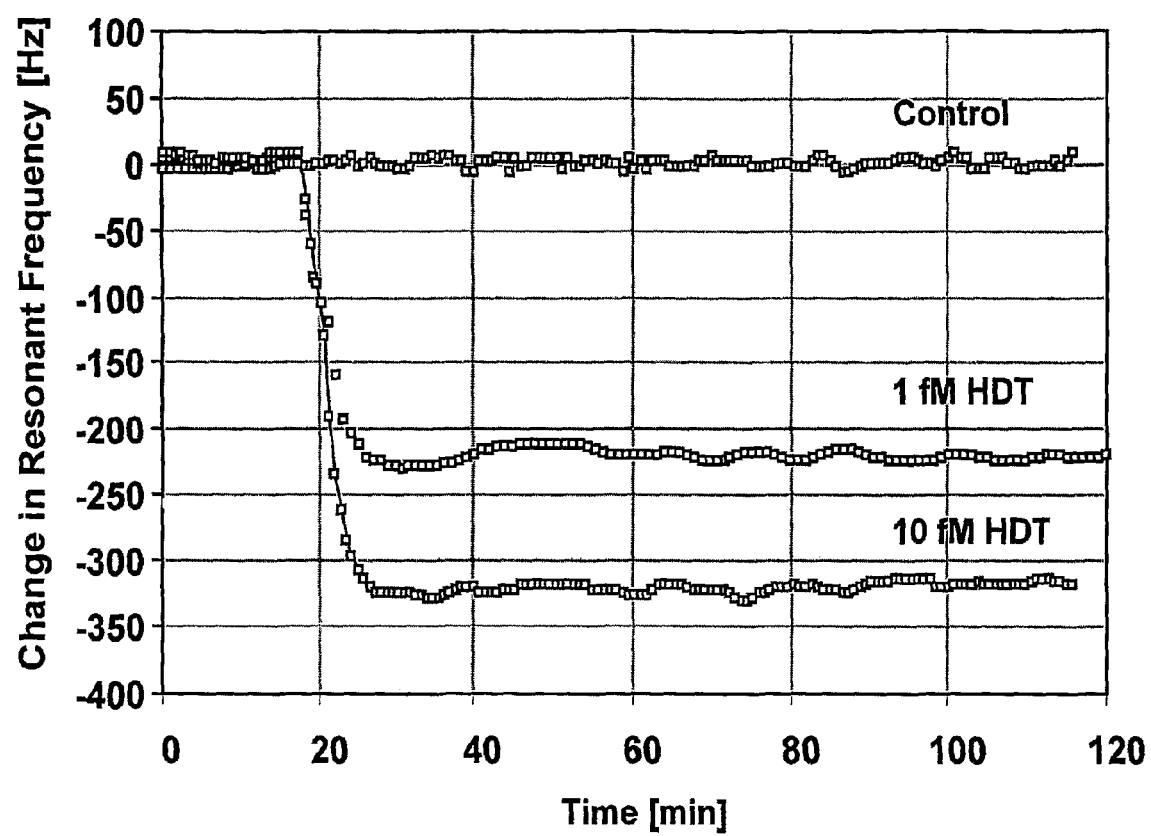
FIG. 14 illustrates a comparison of response to 1 fM and 10 fM 1-hexadecanethiol.

In order to examine if reproducible measurement at 1 fM can be obtained, repeated experiments (n=4) were conducted with PEMC A, after the initial sequential addition studies were completed. As depicted in FIG. 14, response to 1 fM and 10 fM HDT were compared. The raw data were time-shifted to the same thiol addition time so that relative changes could be observed directly. The rates were nearly identical, and both exhibited small oscillations of the order of ±10 Hz, which is thought to be due to small variation (±0.1° C.) in flow cell temperature. Although data were recorded at 2 Hz, the resonance peaks during the run were well-shaped and had a well defined top. In the case of 1 fM, the response reached a lower value and then recovered slightly. It was observed that a less pronounced behavior occurred with 10 fM. The steady state responses were −223±7 and −317±6 Hz with the variation characterized over t=60 to 120 min. A ten-fold increase in concentration caused a 44% increase in resonance frequency. The sensor response is nonlinear. It was concluded that chemisorption of alkanethiols at femtomolar concentration can be measured with reasonable reproducibility. It is was also observed that overall chemisorption rate at such a low concentration is more rapid than 0.1 min$^{+1}$.

In another experiment, to determine if diffusion limits chemisorption of alkanethiol, transport-limited chemisorption was tested for at a low concentration, such as 1 fM. It was determined if flow rate, which enhances transfer rate to the surface, affects the observed chemisorption rate. Chemisorption at 0.6, 0.9 and 1.25 mL/min of 1 fM and 10 fM were measured. Two observations were made. First, the resonance frequency change was similar in all six cases, even though their steady state values showed a weak dependence on flow rate. The higher flow rate (1.25 mL/min) yielded a slightly lower total response compared to the slowest flow rate (0.6 mL/min) for both 1 and 10 fM. At 1 fM, the steady state response varied within 30 Hz, while at 10 fM they were 310, 350 and 390 Hz with a mean of 350 Hz. Since the responses were within 10% of the mean, it was concluded that there was no appreciable difference among the responses since surface cleaning and preparation reproducibility from experiment to experiment ranged from 6 to 10%. The time to reach steady rate for the six cases varied from 6 min at 1.25 mL/min to 14 minutes at 0.6 mL/min. Since the flow rate also altered the time taken to introduce the new concentration into the flow cell, the resonant frequency change with alkanethiol solution residence time in the flow circuit was analyzed, which showed that rate of chemisorption was very slightly more rapid at the 0.6 than at 1.25 mL/min at both 1 and 10 fM. It is believed that the differences are near the experimental error band, and the conclusion is that the chemisorption rate, not transport, limits chemisorption at 1 and 10 fM.

A given alkanethiol concentration gave rise to a surface concentration that reached a constant value as measured by the PEMC sensor. Such a response suggests an equilibrium behavior as in adsorption isotherm. After chemisorption of HDT at a particular concentration, the short term (20-30 min) response to zero, at lower and higher concentration HDT-solutions, was examined. Two experiments were conducted with PEMC B and PEMC. Adsorption of 1 pM HDT resulted in a change of 1,023±8 Hz. After reaching steady state, inflow was changed to pure ethanol which resulted in essentially no change in resonance frequency (−1,031±8 Hz) even after 20 minutes of ethanol flow indicating that chemisorbed HDT did not desorb. Subsequent flow of 100 fM also failed to elicit a response (−1,042±24 Hz). After 25 minutes of flow, when the flow was switched to a higher concentration 10 pM, the resonance frequency decreased and stabilized at −1,365±23 Hz. At 10 pM, the potential surface coverage of the sensor was 1.9%. Finally, when an even higher concentration, 100 pM HDT was introduced, the resonance frequency decreased to −1,919±21 Hz. The results in FIG. 7B are another continuous experiment performed with HDT on the sensor PEMC C. It shows that when pure ethanol was pumped through the flow-cell for 30 minutes after forming a SAM at 1 pM HDT, there was no change in the resonance frequency. Further, when the surface was exposed to a lower concentration (100 fM HDT) no changes in resonance frequency occurred. However, 100 pM solution resulted in a decrease of 1,280±22 Hz. These experiments and others (n=7) lead to the conclusion that surface coverage at low concentration is a function of concentration in the liquid sample and that the chemisorbed HDT is not released in 20-30 minutes when concentration in liquid is lowered. Another observation is that HDT present in a lower concentration solution does not chemisorb onto a surface equilibrated with a higher HDT concentration, even though significant percent of adsorption sites (>99%) is available.

Figure 15A:
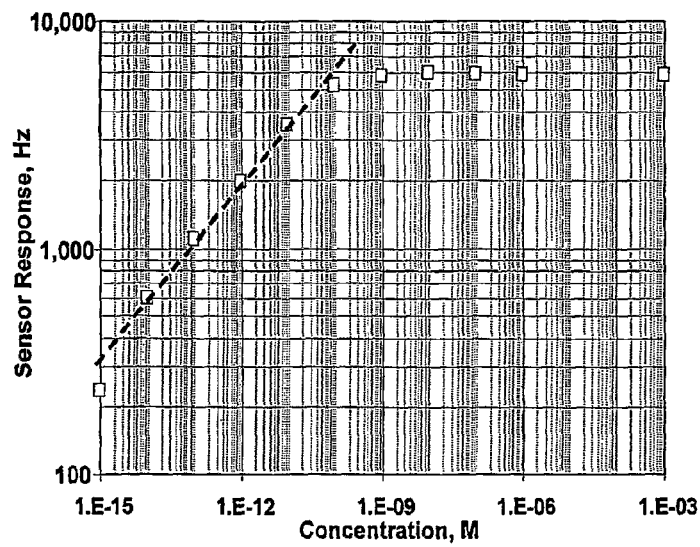
FIG. 15 shows PEMC A sensor response as a function of liquid phase concentration obtained in an experiment.
Figure 15B:
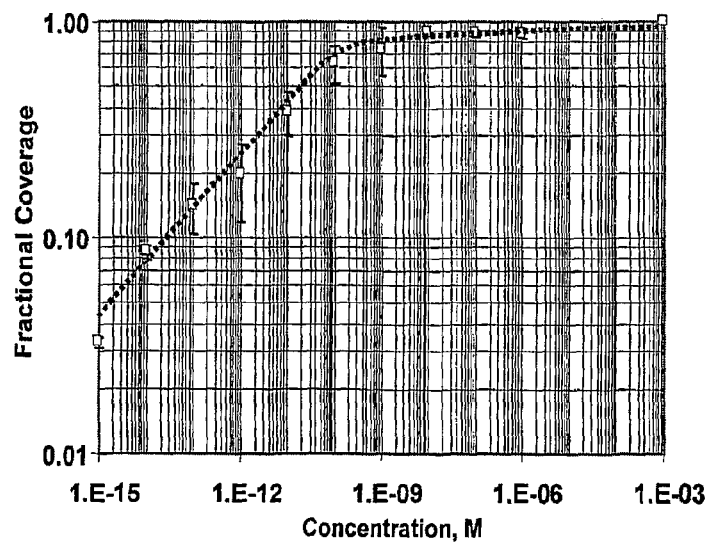

The quantitative relationship between resonance frequency change and 1-hexadecanethiol concentration also was examined. The results are depicted in FIG. 15A and FIG. 15B. The response is determined using cumulative sensor frequency decrease. It is observed that the response is near linear on a log-log plot reaching a constant response value beyond 1 nM due to surface saturation. The dotted line indicates the near linear relationship of sensor response with thiol concentration. Since PEMC sensor response is proportional to attached mass, a ratio of response to the maximum response can be equated to fractional surface coverage. In FIG. 15B a composite response of fractional coverage obtained in multiple experiments with various PEMC sensors (with similar resonance spectrum, but sensitivity variation was ±10%) is given at various HDT concentrations investigated. The experimental data set is large with over 60 experiments. The results can be correlated to concentration as $\log(\theta)=\alpha+\beta \log (C_b^0)$, where $\theta$ is fractional coverage, $C_b^0$ is HDT concentration, $\alpha$ and $\beta$ are constants. The data set in FIG. 8B includes data obtained with PEMC A, B, C, D and E. The sensors D and E were ~10% less sensitive compared to A, B and C. The constants were determined as $\alpha=2$ and $\beta=0.21$, and is plotted in FIG. 15 B. Fractional coverage $\theta=C_b^0/(C_b^0+(1/K_{eq}))$ is related to equilibrium constant ($K_{eq}$) and bulk thiol concentration. The model correlates well with experimental data in cases where fractional coverage change takes place over three orders of magnitude change in The various techniques described herein can be implemented in connection with hardware or software or, where appropriate, with a combination of both. Thus, the methods and apparatuses described herein, or certain aspects or portions thereof, can take the form of program code (i.e., instructions) embodied in tangible media, such as floppy diskettes, CD-ROMs, hard drives, or any other machine-readable storage medium, wherein, when the program code is loaded into and executed by a machine, such as a computer, the machine becomes an apparatus for practicing the invention. The program code can be implemented in a high level procedural or object oriented programming language to communicate with a computer. The program(s) can be implemented in assembly or machine language, if desired. In any case, the language can be a compiled or interpreted language, and combined with hardware implementations.

The program code can be transmitted over a transmission medium, such as over electrical wiring or cabling, through fiber optics, or via any other form of transmission, wherein, when the program code is received and loaded into and executed by a machine, such as an EPROM, a gate array, a programmable logic device (PLD), a client computer, a video recorder, or the like, the receiving machine becomes an apparatus for implementing molecular control of surface coverage. When implemented on a general-purpose processor, the program code combines with the processor to provide a unique apparatus that operates to invoke the functionality of molecular control of surface coverage. Additionally, any storage techniques can invariably be a combination of hardware and software.

While it is envisioned that numerous embodiments of molecular control of surface coverage are particularly well-suited for computerized systems, nothing in this document is intended to limit the invention to such embodiments. On the contrary, as used herein the term "computer system" is intended to encompass any and all devices capable of storing and processing information and/or capable of using the stored information to control the behavior or execution of the device itself, regardless of whether such devices are electronic, mechanical, logical, or virtual in nature.

While illustrative embodiments have various figures, it is to be understood that other similar embodiments can be used or modifications and additions can be made to the described embodiments for performing molecular control of surface coverage without deviating therefrom. Therefore, molecular control of surface coverage should not be limited to any single embodiment, but rather should be construed in breadth and scope in accordance with the appended claims.

What is claimed:

1. A method for determining a surface coverage of a material, the method comprising:
   providing a predetermined concentration of the material; and
   exposing the surface to the provided material until equilibrium is established in a molecular reaction between the surface and the material, wherein:
      the surface comprises a surface of a non-piezoelectric layer of a piezoelectric cantilever sensor, the piezoelectric cantilever sensor comprising:
         a piezoelectric layer comprising a proximate end and a distal end;
         a non-piezoelectric layer comprising a proximate end and a distal end, wherein at least a portion of the piezoelectric layer is coupled to at least a portion of the non-piezoelectric layer such that the piezoelectric layer and the non-piezoelectric layer are not coextensive;
         a base portion coupled to the proximate end of the piezoelectric layer, wherein the base portion is not attached to the proximate end of the non-piezoelectric layer; and
         electrodes operatively associated with the piezoelectric layer; and
      equilibrium is determined in accordance an amount of mass of the material accumulated on the surface.

2. A method in accordance with claim 1, wherein:
   equilibrium is determined by measuring a resonance frequency of the piezoelectric cantilever sensor; and
   a resonance frequency of the piezoelectric cantilever sensor is indicative of an amount mass of the material accumulated on the surface.

3. A method in accordance claim 2, wherein equilibrium is established when a resonance frequency of the piezoelectric cantilever sensor subsequent to exposure to the material differs, by at least a predetermined amount, from a resonance frequency of the piezoelectric cantilever sensor prior to exposure to the material.

4. A method in accordance with claim 1, further comprising determining a concentration of the material on the surface in accordance with an amount of mass of the material accumulated on the surface.

5. A method in accordance with claim 1, further comprising determining a concentration of the material on the surface by measuring a resonance frequency of the piezoelectric cantilever sensor, wherein a resonance frequency of the piezoelectric cantilever sensor is indicative of an amount mass of the material accumulated on the surface.

6. A method in accordance claim 1, further comprising:
   measuring a first resonance frequency of the piezoelectric cantilever sensor prior to exposure to the material;
   measuring a second resonance frequency of the piezoelectric cantilever sensor subsequent to exposure to the material;
   determining that a predetermined concentration of the material is on the surface if the second resonance frequency differs from the first resonance frequency by a predetermined amount.

7. A method in accordance with claim 1, further comprising a concentration of the material on the surface in accordance with:
   the predetermined concentration of the material; and
   an amount time the surface is exposed to the material.

8. A method in accordance with claim 1, further comprising:
   providing predetermined concentrations of a plurality of materials; and
   exposing the surface to the plurality of materials until equilibrium is established, respectively, in a molecular reaction between the surface and each one of the plurality of materials.

9. A method in accordance with claim 8, wherein each of the plurality of materials is sequentially exposed to the surface.

10. A method in accordance with claim 9, further comprising determining a respective concentration of each one of the plurality of materials on the surface in accordance with:
    a respective predetermined concentration of each material; and
    a respective amount time the surface is exposed to each material.

11. A method in accordance with claim 1, wherein equilibrium is indicative of a concentration of the material on the surface.

12. A system for determining a surface coverage of a material, the system comprising:
    a piezoelectric cantilever sensor comprising:
       a piezoelectric layer comprising a proximate end and a distal end;

a non-piezoelectric layer comprising a proximate end and a distal end, wherein:
at least a portion of the piezoelectric layer is coupled to at least a portion of the non-piezoelectric layer such that the piezoelectric layer and the non-piezoelectric layer are not coextensive; a base portion coupled to the proximate end of the piezoelectric layer: and
the base portion is not attached to the proximate end of the non-piezoelectric layer;
an exposing portion configured to expose a predetermined concentration of the material to the surface until equilibrium is established in a molecular reaction between the surface and the material, wherein:
the surface comprises a surface of the non-piezoelectric layer of the piezoelectric cantilever sensor; and
equilibrium is determined in accordance an amount of mass of the material accumulated on the surface.

13. A system in accordance with claim 12, wherein:
equilibrium is determined by measuring a resonance frequency of the piezoelectric cantilever sensor; and
a resonance frequency of the piezoelectric cantilever sensor is indicative of an amount mass of the material accumulated on the surface.

14. A system in accordance claim 13, wherein equilibrium is established when a resonance frequency of the piezoelectric cantilever sensor subsequent to exposure to the material differs, by at least a predetermined amount, from a resonance frequency of the piezoelectric cantilever sensor prior to exposure to the material.

15. A system in accordance with claim 12, further comprising a processing portion configured to determine a concentration of the material on the surface in accordance with an amount of mass of the material accumulated on the surface.

16. A system in accordance with claim 12, further comprising a processing portion configured to determine a concentration of the material on the surface by measuring a resonance frequency of the piezoelectric cantilever sensor, wherein a resonance frequency of the piezoelectric cantilever sensor is indicative of an amount mass of the material accumulated on the surface.

17. A system in accordance claim 12, further comprising a processing portion configured to:
measure a first resonance frequency of the piezoelectric cantilever sensor prior to exposure to the material;
measure a second resonance frequency of the piezoelectric cantilever sensor subsequent to exposure to the material;
determine that a predetermined concentration of the material is on the surface if the second resonance frequency differs from the first resonance frequency by a predetermined amount.

18. A system in accordance with claim 12, further comprising a processing portion configured to determine a concentration of the material on the surface in accordance with:
the predetermined concentration of the material; and
an amount time the surface is exposed to the material.

19. A system in accordance with claim 12, further configured to:
expose predetermined concentrations of a plurality of materials to the surface until equilibrium is established, respectively, in a molecular reaction between the surface and each one of the plurality of materials.

20. A system in accordance with claim 19, wherein each of the plurality of materials is sequentially exposed to the surface.

21. A system in accordance with claim 20, further comprising a processing portion configured to determine a respective concentration of each one of the plurality of materials on the surface in accordance with:
a respective predetermined concentration of each material; and
a respective amount time the surface is exposed to each material.

22. A system in accordance with claim 12, wherein equilibrium is indicative of a concentration of the material on the surface.

23. A method for coating a surface with a material, the method comprising:
providing a predetermined concentration of the material; and
exposing the surface to the provided material for a predetermined amount of time, wherein:
the surface comprises a predetermined surface area of an attractor for attracting the material; and
within the predetermined amount of time, equilibrium is established in a molecular reaction between the attractor and the material; and
determining, utilizing a piezoelectric cantilever sensor, that an amount of the material attached to the attractor resulting from equilibrium is less than a total amount of material attractable to the attractor, the piezoelectric cantilever sensor comprising:
a piezoelectric layer comprising a proximate end and a distal end;
a non-piezoelectric layer comprising a proximate end and a distal end, wherein at least a portion of the piezoelectric layer is coupled to at least a portion of the non-piezoelectric layer such that the piezoelectric layer and the non-piezoelectric layer are not coextensive;
a base portion coupled to the proximate end of the piezoelectric layer, wherein the base portion is not attached to the proximate end of the non-piezoelectric layer.

24. A method in accordance with claim 23, further comprising sequentially exposing the surface to at least one other material, respectively, wherein each subsequent exposure results in coating an uncoated surface area of the attractor.

25. A method in accordance with claim 23, wherein the surface comprises a plurality of attractors for respectively attracting a plurality of materials.

* * * * *